(12) United States Patent
Fletcher et al.

(10) Patent No.: US 9,149,666 B2
(45) Date of Patent: Oct. 6, 2015

(54) FAST ACTING SNARE-CLEAVING ENZYMES

(75) Inventors: Paul L. Fletcher, Greenville, NC (US);
Maryann D. Fletcher, Greenville, NC (US); Brian M. Martin, Rockville, MD (US)

(73) Assignees: East Carolina University, Greenville, NC (US); National Institutes of Health, Rockville, MD (US)

( * ) Notice: Subject to any disclaimer, the term of this patent is extended or adjusted under 35 U.S.C. 154(b) by 784 days.

(21) Appl. No.: 13/390,674

(22) PCT Filed: Aug. 17, 2010

(86) PCT No.: PCT/US2010/045701
§ 371 (c)(1),
(2), (4) Date: May 17, 2012

(87) PCT Pub. No.: WO2011/022357
PCT Pub. Date: Feb. 24, 2011

(65) Prior Publication Data
US 2012/0225049 A1 Sep. 6, 2012

(51) Int. Cl.
| | |
|---|---|
| C12N 9/64 | (2006.01) |
| A61Q 19/08 | (2006.01) |
| A61K 38/48 | (2006.01) |
| A61K 8/60 | (2006.01) |
| A61K 8/64 | (2006.01) |
| A61K 8/66 | (2006.01) |
| A61K 38/00 | (2006.01) |

(52) U.S. Cl.
CPC ............... *A61Q 19/08* (2013.01); *A61K 8/606* (2013.01); *A61K 8/64* (2013.01); *A61K 8/66* (2013.01); *A61K 38/48* (2013.01); *A61K 38/4886* (2013.01); *C12N 9/6402* (2013.01); *C12N 9/6416* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,776,990 | B2 | 8/2004 | Sachs et al. |
| 6,908,925 | B2 | 6/2005 | Breton et al. |
| 7,456,272 | B2 | 11/2008 | Lin et al. |
| 2005/0019346 | A1 | 1/2005 | Boulis |
| 2008/0319167 | A1 | 12/2008 | Foster et al. |

FOREIGN PATENT DOCUMENTS

WO WO 2004-080471 A1 9/2004

OTHER PUBLICATIONS

Novello et al., "TsTX-IV, a short chain four-disulfide-bridged neurotoxin from Tityus serrulatus venom which acts on Ca2+-activated K+ channels", Toxicon, vol. 37, pp. 651-660, 1999.*
Teixeira et al., "Sequence and structure-activity relationship of a scorpion venom toxin with nitrergic activity in rabbit corpus cavernosum", FASEB Journal, vol. 17, pp. 485-487, 2003.*

(Continued)

*Primary Examiner* —

(56) References Cited

OTHER PUBLICATIONS

Martin et al., "Purification and chemical and biological characterizations of seven toxins from the Mexican scorpion, Centruroides suffusus suffusus", Journal of Biological Chemistry, vol. 262, No. 10, pp. 4452-4459, 1987.*
Cologna et al., "Tityus serrulatus Scorpion Venom and Toxins: An Overview", Protein and Peptide Letters, Bentham Science Publishers, Jan. 1, 2009, vol. 16, No. 8, pp. 920-932.
Fletcher et al., "Exocrine Pancreatic Secretion and Effects on SNARE Components by Scorpion Venom", Molecular Biology of the Cell, American Society for Cell Biology, Jan. 1, 2007, vol. 18, pp. 272a.
Holaday et al., "NMR Solution Structure of Butantoxin", Archives of Biochemistry and Biophysics, Jul. 1, 2000, vol. 379, No. 1, pp. 18-27.
Possani et al., "Discharge Effect on Pancreatic Exocrine Secretion Produced by Toxins Purified from Tityus serrulatus Scorpion Venom", Journal of Biological Chemistry, Jan. 1, 1991, vol. 266, No. 5, pp. 3178-3185.
Possani et al., "Purification and Properties of Mammalian Toxins From the Venom of the Brazilian Scorpion Tityus serrulatus Lutz and Mello", Archives of Biochemistry and Biophysics, Academic Press, Apr. 30, 1977, vol. 180, No. 2, pp. 394-403.
Extended European Search Report in corresponding European Application No. EP 10 81 0460, mailed Apr. 18, 2013 (5 pages).
Bartholomew, C. "Acute Scorpion Pancreatitis in Trinidad", British Medical Journal, vol. 1, 1970, pp. 666-668.
Brunger, A.T. et al., "Highly specific interactions between botulinum neurotoxins and synaptic vesicle proteins", Cellular and Molecular Life Sciences, vol. 65, 2008, pp. 2296-2306.
Cheng, C.M. et al., "Unlabeled uses of botulinum toxins: A review, part 1", Am J Health-Syst Pharm, vol. 63, Jan. 15, 2006, pp. 145-152.
Fletcher, M.D. et al., "Morphological studies by light and electron microscopy of pancreatic acinar cells under the effect of Tityus serrulatus venom", Cell Tussue Res., vol. 278, 1994, pp. 255-264.
Fletcher, P.L. et al., "Characteristics of pancreatic exocrine secretion produced by venom from the Brazilian scorpion, Tityus serrulatus", European Journal of Cell Biology, vol. 58, 1992, pp. 259-270.
Gwee, M. CE. et al., "Autonomic Effects of Some Scorpion Venoms and Toxins", Clinical and Experimental Pharmacology and Physiology, vol. 29, 2002, pp. 795-801.
International Preliminary Report on Patentability Corresponding to International Application No. PCT/US2010/045701; Date of Mailing: Mar. 1, 2012; 7 pages.
Ismail, M., "The Scorpion Envenoming Syndrome", Toxicon, vol. 33, No. 7, 1995, pp. 825-858.
Klöppel, G. et al., "Human acute pancreatitis: its pathogenesis in the light of immunocytochemical and ultrastructural findings in acinar cells", Virchows Arch A, vol. 409, 1986, pp. 791-803.
Pessini, A.C. et al., "A hyaluronidase from Tityus serrulatus scorpion venom: isolation, characterization and inhibition by flavonoids", Toxicon, vol. 39, 2001, pp. 1495-1504.
Possani, L.D. et al., "Discharge Effect on Pancreatic Exocrine Secretion Produced by Toxins Purified from Tityus serrulatus Scorpion Venom", The Journal of Biological Chemistry, vol. 266, No. 5, Feb. 15, 1991, pp. 3178-3185.
Possani, L.D. et al., "Purification and Properties of Mammalian Toxins from the Venom of the Brazilian Scorpion Tityus serrulatus Lutz and Mello", Archives of Biochemistry and Biophysics, vol. 180, 1977, 394-403.
Rosado, J.A. et al., "Cleavage of SNAP-25 and VAMP-2 impairs store-operated Ca 2+ entry in mouse pancreatic acinar cells", Am J Physiol Cell Physiol, vol. 288, 2005, pp. 214-221.
Söllner, T. et al., "SNAP receptors implicated in vesicle targeting and fusion", Nature, vol. 362, Mar. 25, 1993, pp. 318-324.
Wang, C.C. et al., "A Role of VAMP8/Endobrevin in regulated Exocytosis of Pancreatic Acinar Cells", Developmental Cell, vol. 7, Sep. 2004, pp. 359-371.
Waterman, J.A., "Some Notes on Scorpion Poisoning in Trinidad", Transactions of the Royal Society of Tropical Medicine and Hygiene, vol. 31, No. 6, Apr. 1938, pp. 607-624.
Notification of Transmittal of the International Search Report and the Written Opinion of the International Searching Authority, or the Declaration in corresponding PCT Application No. PCT/US2010/045701 mailed Apr. 25, 2011 (13 pages).
Fletcher et al. "Vesicle-associated membrane protein (VAMP) cleavage by a new metalloprotease from the Brazilian scorpion tityus serrulatus" The Journal of Biological Chemistry, vol. 285(10), pp. 7405-7416 (Dec. 21, 2009).
Chen, "Clinical Uses of Botulinum Neurotoxins: Current Indications, Limitations and Future Developments," Toxins, 4:913-939, (2012) p. 914.
Cox et al., "QnabotulinumtoxinA for the treatment of overactive bladder," Research and Reports in Urology, 6:79-89 (2014), abstract.
Fairweather et al., "Mast Cells and Inflammatory Heart Disease: Potential Drug Targets," Cardiovascular & Haematological Disorders—Drug Targets, 8(1):80-90 (2008).
Ilie et al., "Perspective of Botox for treatment of male lower urinary tract symptoms," Current Opinion in Urology, 19:20-25, (2009).
Jones et al., "VAMP8 is a vesicle SNARE that regulates mucin secretion in airway goblet cells," The Journal of Physiology, 590(3):545-561 (2012).
Kammerer et al., "Botulinum neurotoxins: new questions arising from structural biology," Trends in Biochemical Sciences, 39(11):517-526 (2014).
Sander et al., "Vesicle associated membrane protein (VAMP)-7 and VAMP-8, but not VAMP-2 or VAMP-3, are required for activation-induced degranulation of mature human mast cells," European Journal of Immunology, 38:855-863 (2008).
Valdez-Velazquez et al., "Mass Fingerprinting of the Venom and Transcriptome of Venom Gland of Scorpion Centruroides tecomanus," PLOS ONE, 8(6): 1-15, (Jun. 2013).
Woska et al., "Small-Interfering RNA-Mediated Identification and Regulation of the Ternary SNARE Complex Mediating RBL-2H3 Mast Cell Degranulation," Scandinavian Journal of Immunology, 73(1):8-17 (2011).
Zhu et al., "Dual Role of VAMP8 in Regulating Insulin Exocytosis and Islet β Cell Growth," Cell Metabolism, 16(2):238-249 (2012).
Zong et al., "Enhanced Energy Expenditure, Glucose Utilization, and Insulin Sensitivity in VAMP8 Null Mice," Diabetes, 60(1):30-38 (2011).

* cited by examiner

```
              10         20         30         40         50
AnI    SPCLLIDYLC VTETTFTERF KTNKELLEYI TVMFTGVQNL LDTLNLGIKA
       ||:::|:   ||::  |·| || :|| | :|: ||||||||:| |||||||||:
AnII   DDDCIVVEYYI VTDSAFTKRF KSNSALTNYV TVMFTGVQEL LDTLNLGIGV
       | |||||  :  ||:||||||| ||||||  |||·||||||  ·|||·||||
AzI    KDQCIVVECLV VTESAFTKRF ETTKALTEYV TVMYTGVQNL IDTLQLGIKF
       ||:|:|||  :|| |||||
AzII   SGKCIIVDCLV LTENAFTKR  xxxxxxxx>

60         70         80         90        100
AnI    QVIGITPFKK QNEPSFIEDS AIPGHQQVLD PVDLVKNMAK YYCNNAKGLA
       ::|:|:|  x x ||||||||. ||||    ..| |xx|:  | |  |||| ·|||
AnII   RLLGVTTFTE KTEPSFIKDN LIPGPPAAFD PDVLISAMSK YYCNHQTGLA
       ||||: ·||x x||| :|... · |   |   .: |xx|:  | |  ||||·|||
AzI    RLLGIDPFTK ETEPPYIEES ANPVNPKYLN PLDLIDRMGK YYCNHATGLA 110        120        130        140        150
AnI    KDADIIMLIS NRKLGELQDD GTVAYNTAGI SLGSGVCKQC SKVGVAQDDS
       ||||||:||:   | :|:|.:| ||| :||||| : xx||||:| |:|:| |||
AnII   KDTDLIFLIT ARGMGDPRED GTVDINTAGI ANSAGVCKPC FKSGIATDDS
       ||·| |||:   | :|:.::| ||| : |: |   xx||||:| :|:||| |||
AzI    KDADMIMLLV TRNLGELKDD GTVKFRVVGL AYKGAVCKQC YKVGVCKDDS 160        170        180        190        200
AnI    DYNERVDTVA HETAHLIGAP HDEEGPxxxx xxxxxxxxxx xSDGYIMGSG
       ||||||||:|  ||::||||:| || |||                 :|||||
AnII   DYNERVDTLA HESVHLLGSP HDGEGPNLVS LGSPGAANCP AKAGYIMGNR
       ||||||||:|  |||:||||||  |||xx                |:|||||||
AzI    YYNERVDTVA HESAHLLGSP HDGEPGAxxx xxxxxxxxxx xKDGYIMGNR 210        220        230
AnI    NNKVNKFKFS KCTKKCVEHL LSLPRASCVL ADC         233
       |:||||:||| :|||||||| | ||:| |||:.  :|
AnII   NDKVNKYKFS NCTKKCVEYL LSKPTASCIF QQCSD       235
       |||||||||| :|||||| :  ||:| | |::  · |    Mw = 25,500
AzI    RDKVNKYKFS KCTKKCVKDA LSLPEAKCVY ESCG  C-term 234
```

Fig. 10

A. Antarease II (AnII)

```
                    10         20         30         40         50
AnII        DDDCIVVEYYI VTDSAFTKRF KSNSALTNYV TVMFTGVQEL LDTLNLGIGV 60         70         80         90        100
AnII        RLLGVTTFTE KTEPSFIKDN LIPGPPAAFD PDVLISAMSK YYCNHQTGLA 110        120        130        140        150
AnII        KDTDLIFLIT ARGMGDPRED GTVDINTAGI ANSAGVCKPC FKSGIATDDS 160        170        180        190        200
AnII        DYNERVDTLA HESVHLLGSP HDGEGPNLVS LGSPGAANCP AKAGYIMGNR 210        220        230        240
AnII        NDKVNKYKFS NCTKKCVEYL LSKPTASCIF QQCSD         235
SEQ ID NO:2;  Mw = 25,500              lc - 2     x - 16
```

DDDCIVVEYYIVTDSAFTKRFKSNSALTNYVTVMFTGVQELLDTLNLGIGV
RLLGVTTFTEKTEPSFIKDNLIPGPPAAFDPDVLISAMSKYYCNHQTGLA
KDTDLIFLITARGMGDPREDGTVDINTAGIANSAGVCKPCFKSGIATDDS
DYNERVDTLAHESVHLLGSPHDGEGPNLVSLGSPGAANCPAKAGYIMGNR
NDKVNKYKFSNCTKKCVEYLLSKPTASCIFQQCSD   SEQ ID NO:2

B. A reverse translation of ANII:

gatgatgattgcattgtggtggaatattatattgtgaccgatagcgcgtttaccaaacgc
tttaaaagcaacagcgcgctgaccaactatgtgaccgtgatgtttaccggcgtgcaggaa
ctgctggatacccgaacctgggcattggcgtgcgcctgctgggcgtgaccacctttacc
gaaaaaaccgaaccgagctttattaaagataacctgattccgggcccgccggcggcgttt
gatccggatgtgctgattagcgcgatgagcaaatattattgcaaccatcagaccggcctg
gcgaaagataccgatctgatttttctgattaccgcgcgcggcatgggcgatccgcgcgaa
gatggcaccgtggatattaacaccgcgggcattgcgaacagcgcgggcgtgtgcaaaccg
tgctttaaaagcggcattgcgaccgatgatagcgattataacaacgcgtggatacctg
gcgcatgaaagcgtgcatctgctgggcagcccgcatgatggcgaaggcccgaacctggtg
agcctgggcagcccgggcgcggcgaactgccggcgaaagcgggctatattatgggcaac
cgcaacgataaagtgaacaaatataaatttagcaactgcaccaaaaaatgcgtggaatat
ctgctgagcaaaccgaccgcgagctgcatttttcagcagtgcagcgat   SEQ ID NO:9

C. A second reverse translation of ANII:

gaygaygaytgyathgtngtngartaytayathgtnacngaywsngcnttyacnaarmgn
ttyaarwsnaaywsngcnytnacnaaytaygtnacngtnatgttyacnggngtncargar
ytnytngayacnytnaayytnggnathggngtnmgnytnytnggngtnacnacnttyacn
garaaracngarccnwsnttyathaargayaayytnathccnggnccnccngcngcntty
gayccngaygtnytnathwsngcnatgwsnaartaytaytgyaaycaycaracnggnytn
gcnaargayacngayytnathttyytnathacngcnmgnggnatgggngayccnmgngar
gayggnacngtngayathaayacngcnggnathgcnaaywsngcnggngtntgyaarccn
tgyttyaarwsnggnathgcnacngaygaywsngaytayaaygarmgngtngayacnytn
gcncaygarwsngtncayytnytnggnwsnccncaygayggngarggnccnaayytngtn
wsnytnggnwsnccnggngcngcnaaytgyccngcnaargcnggntayathatgggnaay
mgnaaygayaargtnaayaartayaarttywsnaaytgyacnaaraartgygtngartay
ytnytnwsnaarccnacngcnwsntgyathttycarcartgywsngay   SEQ ID NO:10

Fig. 11

FAST ACTING SNARE-CLEAVING ENZYMES

STATEMENT OF PRIORITY

This application is a 35 U.S.C. §371 national phase application of International Application Serial No. PCT/US2010/045701, filed Aug. 17, 2010, which claims the benefit, under 35 U.S.C. §119 (e), of U.S. Provisional Application No. 61/234,429, filed Aug. 17, 2009, the entire contents of which are incorporated by reference herein.

STATEMENT REGARDING ELECTRONIC FILING OF A SEQUENCE LISTING

A Sequence Listing in ASCII text format, submitted under 37 C.F.R. §1.821, entitled 5218-186ST25.txt, 23,437 bytes in size, generated on Jan. 20, 2015 and filed via EFS-Web, is provided in lieu of a paper copy. This Sequence Listing is hereby incorporated by reference into the specification for its disclosures.

FIELD OF THE INVENTION

The present invention provides metalloprotease enzymes isolated from scorpion venom that cleave SNARE complex proteins, their nucleic acid and amino acid sequences, and methods of use thereof in the treatment of various diseases, disorders and cosmetic conditions.

BACKGROUND OF THE INVENTION

Eukaryotic intracompartmental transport and secretory processes require fusion of vesicles with cellular membranes (1, 2, 3). A step leading to fusion of vesicles with cellular membranes is assembly of a tetrameric coiled-coil structure formed from sets of membrane proteins known as SNAREs (4) (soluble N-ethyl maleimide sensitive factor attachment protein receptors) (4). High-resolution structures are available for the final, post-fusion ternary SNARE complex that combines one vesicle protein (v-SNARE) with two target membrane proteins (t-SNARES). The SNAREs responsible for neuronal secretion are among the best-studied examples of this family of proteins. They include the v-SNARE VAMP (vesicle-associated membrane protein) that is located on the secretory vesicle membrane and two t-SNAREs—syntaxin (sx) and SNAP25 (synaptosomal-associated protein 25) present on the target membrane (5, 6).

SNAREs are responsible for selective transport between cellular compartments (7, 8). Alterations or damage to proteins or membranes that perform integral transport functions often produce disabling or irreversible consequences. Failure of the normal vesicular traffic (unless transient), which is the basis for intracellular transport and secretion, results in development of disease (9, 10). As a consequence, toxins that attack this machinery have significant effects on normal cellular processes.

Proteolytic cleavage of SNARE family components is currently known to be associated only with large microbial proteins from the genus *Clostridium*. These clostridial proteins require intracellular cleavage before they are released as smaller active proteolytic enzymes (23, 24, 25, 26). The present inventors have identified and isolated enzymes from scorpion venom that cleave also the SNARE complex proteins. These enzymes are unique from the clostridial enzymes with respect to their mechanism of cleavage, specific cleavage targets as well as their structure.

SUMMARY OF THE INVENTION

The present invention provides, in one aspect, an isolated polypeptide comprising an amino acid sequence selected from the group consisting of (1) SEQ ID NO:1, (2) SEQ ID NO:2, (3) SEQ ID NO:3, (4) SEQ ID NO:4, (5) SEQ ID NO:5 and SEQ ID NO:6, (6) SEQ ID NO:7 and SEQ ID NO:8, and a biologically active fragment thereof.

In other aspects, the present invention provides an isolated nucleic acid encoding a polypeptide comprising an amino acid sequence selected from the group consisting of (1) SEQ ID NO:1, (2) SEQ ID NO:2, (3) SEQ ID NO:3, (4) SEQ ID NO:4, (5) SEQ ID NO:5 and SEQ ID NO:6 and (6) SEQ ID NO:7 and SEQ ID NO:8.

In some aspects of the invention an isolated nucleic acid encoding a nucleotide sequence is provided, which is selected from the group consisting of: (a) the nucleotide sequence encoding a polypeptide comprising the amino acid sequence of (1) SEQ ID NO:1, (2) SEQ ID NO:2, (3) SEQ ID NO:3, (4) SEQ ID NO:4, (5) SEQ ID NO:5 and SEQ ID NO:6 or (6) SEQ ID NO:7 and SEQ ID NO:8; (b) a nucleotide sequence having at least 80% sequence identity to (a) above; and (c) a nucleotide sequence that differs from the nucleotide sequences of (a) or (b) above due to the degeneracy of the genetic code.

Further aspects of this invention include an isolated nucleic acid encoding a nucleotide sequence selected from the group consisting of: (a) the nucleotide sequence of SEQ ID NO:9 and SEQ ID NO:10; (b) a nucleotide sequence having at least 80% sequence identity to (a) above; and (c) a nucleotide sequence that differs from the nucleotide sequences of (a) or (b) above due to the degeneracy of the genetic code.

A further aspect of the present invention is a composition comprising an isolated polypeptide of the present invention in a pharmaceutically acceptable carrier.

Another aspect of the invention is a composition comprising an isolated nucleic acid of the invention in a pharmaceutically acceptable carrier.

In addition, the present invention provides methods of treating spasmodic muscles in a subject by administering to said subject an effective amount of a composition of the present invention as described herein.

In some embodiments, a method of treating and/or preventing a cosmetic condition in a subject, comprising administering to the subject an effective amount of a composition described herein, wherein the cosmetic condition is selected from the group consisting of frown wrinkles, forehead wrinkles, wrinkles around the eye (crow's feet), nose crease wrinkles, and combinations thereof.

Further provided is a method of treating and/or preventing a disorder in a subject, comprising administering to the subject an effective amount of a composition of the present invention as described herein, wherein the disorder is selected from the group consisting of strabismus, blepharospasm, headache pain including pain due to a migraine headache, cervical dystonia, severe primary axillary hyperhidrosis, prostatic symptoms, asthma, stroke symptoms, diabetes, obstructive pulmonary disease, achalasia, and combinations thereof.

These and other aspects of the invention will be set forth in more detail in the description of the invention that follows.

BRIEF DESCRIPTION OF THE FIGURES

FIG. 1A shows dose-response curves for TSV, Fx v (Fraction v), Fx λ, (Fraction λ) effects on secretion of radiolabeled (newly-synthesized) proteins. FIG. 1B shows Western blots for phosphotyrosine (PY20), VAMP2 and VAMP3 illustrating TSV dose effect on VAMP and PY20 degradation. The TSV doses of 50 µg/ml and 5 µg/ml are hyperstimulatory for secretion. The 1 µg/ml dose is optimal (see FIG. 1A). Control lobules are in Krebs Ringer Bicarbonate (KRB). FIG. 1C shows the time-course for incubations at two temperatures. TSV concentration is 50 µg/ml. FIG. 1D shows Western blots for VAMP2 and VAMP8 in lobules incubated for 3 hours in optimal stimulatory doses for carbachol (CARE) (10 µM), caerulein (CAER) (1 nM) and hyperstimulatory Tx γ (secretagogue toxin gamma) dose (100 nM) and TSV. For samples in FIGS. 1B, C and D, n=4 or 2 experiments with duplicate flasks.

FIG. 2A shows the unstimulated control. Zymogen granules (ZG) are positively immunostained for VAMP2 shown as 10 nm gold (Au) particles (arrows). FIG. 2B illustrates hyperstimulation with 100 µg/ml TSV. The absence of Au particles signifies the loss of VAMP2. FIG. 2C shows that optimal stimulation with 10 µM carbachol retains VAMP2. FIG. 2D shows that maximal stimulation with 1.0 µg/ml TSV indicates VAMP2 is conserved but fewer Au particles are present. FIG. 2E shows negative primary Ab using unstimulated control. L=acinar lumen. FIG. 2F: Bar graph of statistical analysis of Au distribution. The number of micrographs analyzed for each condition were: A: 23, B: 22, C: 10, D: 30, E: 12. Scale Bars: 0.5 µm.

FIG. 3A shows the effect of 50 µg/ml TSV on VAMP2 in isolated pancreatic ZG; FIG. 3B shows the effect of 50 µg/ml TSV on VAMP2 in isolated pancreatic ZGM. FIG. 3C shows the effect of 10 µg/ml Fx ν on VAMP8. FIG. 3D shows the effects of 50 µg/ml TSV and 10 µg/ml Fx ν on VAMP2 and tyrosine phosphorylation (PY20) in isolated ZG in vitro. Number of experiments: ZG, n=10. ZGM, n=4.

FIG. 4A: 10 µM VAMP2 proteins incubated in vitro at 37° C. for 30 min with 10 µg/ml TSV or 50 µg/ml Fx ν or Fx λ. WT: Wild Type rat VAMP2 cytoplasmic portion 1-94. E41C: Mutant rat VAMP2 cytoplasmic portion 1-94. FIG. 4B: Inhibition of 10 µg/ml Fx ν proteolytic activity by 60 min pre-incubation with 10 mM EDTA, pH 7, in vitro at 37° C. 10 µM VAMP2 1-94 proteins were then added for further 60 min incubation. FIG. 4C: VAMP2 proteins incubated in vitro at 37° C. for 30 min with Fx ν. WT: Wild Type 10 µM rat VAMP2 cytoplasmic portion 1-96, K85A-R86S-K87A: Mutant 10 µM rat VAMP2 cytoplasmic portion 1-96 with altered cleavage site. FIG. 4D: Time-course for WT 10 µM VAMP2 cleavage by 10 µg/ml Fx ν at 37° C. FIG. 4E: 10 µM VAMP2 cleavage during incubation in vitro at 37° C. for 30 min with 50 µg/ml Centruroides sculpturatus venom (CSV). The number of experiments under various conditions for each SNARE protein was as follows: WT V2 1-94, n=20; V2 E41C, n=11; WT V2 1-96, n=9; V2 K85A-R86S-K87A, n=3.

FIG. 5A: 10 µg/ml Fx ν cleaved VAMP2 peptides with sequences. FIG. 5B: Incubated control WT VAMP2.

FIG. 9A shows the size exclusion separation of *Tityus serrulatus* whole venom with Sephadex G-50. FIG. 9B shows the anion exchange chromatographic isolation of Fx ν metalloproteases. Pools I, II, III, IV, and Pool III fractions 1-9 were incubated with WT 20 µM VAMP2 1-96 in vitro at 37° C. for 30 minutes to detect protease activity. Insets are transblots of incubation samples.

FIG. 10 shows an alignment of the amino acid sequences for two proteins isolated from *Tityus serrulatus* (TSV) designated AnI (Antarease I) (SEQ ID NO:1) and AnII (Antarease II) (SEQ ID NO:2) and two proteins isolated from *Centruroides sculpturatus* (CSV) designated AzI (Azantarease I) (SEQ ID NO:3) and AzII (Azantarease II) (SEQ ID NO:4). Compare AnI and AnII: Same=122; Similar:=36; AnI x=14; Compare Ann and AzI: Same=113; Similar:=24; Ann x=15; AzI x=36.

FIGS. 11A-C show (FIG. 11A) the amino acid sequence of Antarease II (SEQ ID NO:2) and two reverse translations (FIGS. 11B and C) (SEQ ID NO:9 and SEQ ID NO:10) of the amino acid sequence of SEQ ID NO:2. FIG. 11B shows the reverse translation of An II to a 708 base sequence of most likely codons (SEQ ID NO:9) and FIG. 11C shows the reverse translation of An II to a 708 base sequence of consensus codons (SEQ ID NO:10).

DETAILED DESCRIPTION

Figure 1:
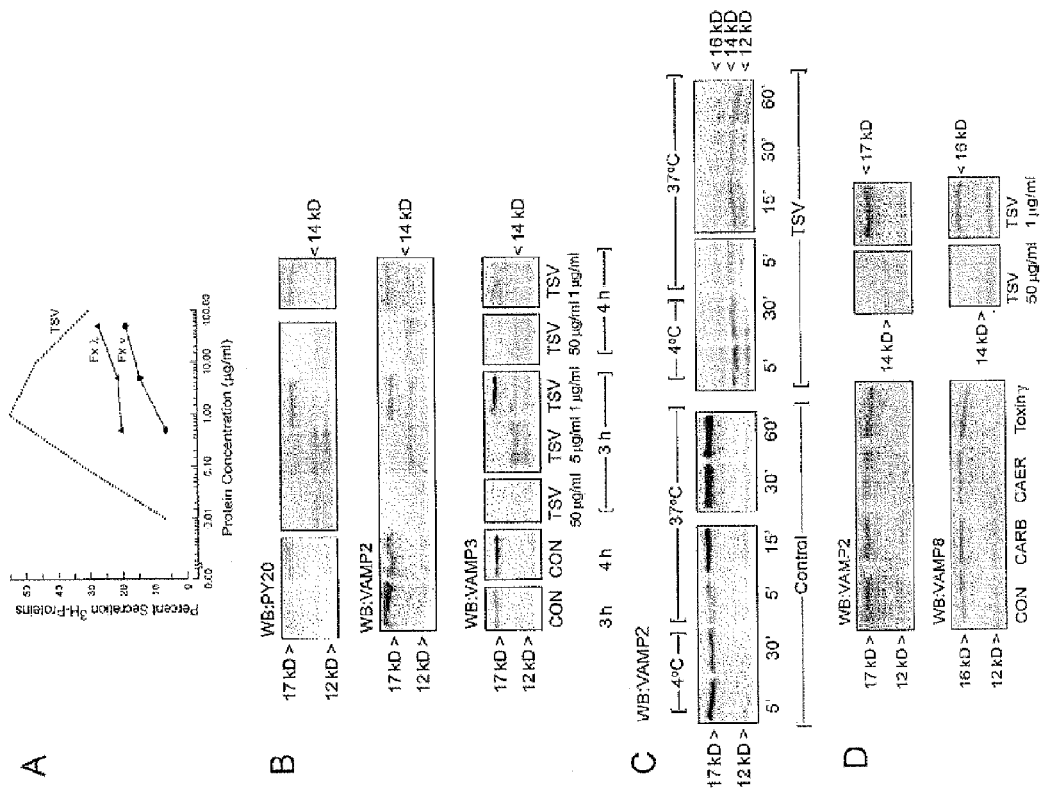
FIGS. 1A-D illustrate TSV (*Tityus serrulatus* venom) cleavage of synaptobrevins in pancreatic lobules in vitro.

Particular aspects of this invention are explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure that do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even 0.1% of the specified amount.

As used herein, the terms "protein" and "polypeptide" are used interchangeably and encompass peptides, unless indicated otherwise. In the protein sequences presented herein, the one-letter code X, x, Xaa or xaa refers to an amino acid that is optionally present or absent and can be any naturally occurring amino acid.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. Polypeptides, proteins, and peptides may comprise naturally occurring amino acids, non-naturally occurring amino acids, or a combination of both. The polypeptides, proteins, and peptides may be isolated from sources (e.g., cells or tissues) in which they naturally occur, produced recombinantly in cells in vivo or in vitro or in a test tube in vitro, or synthesized chemically. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention (e.g., cleavage of SNARE complex proteins) according to the methods described herein, which are routine methods for testing activities of polypeptides, and/or according to any art-known and routine methods for identifying such activities. The production and testing to identify biologically active fragments of the polypeptides described herein would be well within the scope of one of ordinary skill in the art and would be routine. Thus, the present invention further provides biologically active fragments of the polypeptides of the present invention and the polynucleotides encoding such biologically active polypeptide fragments.

As used herein, "nucleic acid," "nucleotide sequence" and "polynucleotide" refer to a chain of nucleotides without regard to length of the chain and encompass both RNA and DNA, including cDNA, genomic DNA, mRNA, synthetic (e.g., chemically synthesized) DNA and chimeras of RNA and DNA [e.g., DNA-RNA hybrid sequences (including both naturally occurring and non-naturally occurring nucleotides)], but are typically either single or double stranded DNA or RNA sequences. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid or nucleotide sequence of this invention.

The nomenclature used in the nucleotide sequences presented herein follows that of the International Union of Biochemistry and Molecular Biology (IUBMB) (www.chem.qmul.ac.uldiubmb/). Thus, G, A, T, C refers to guanine, adenine, thymine, cytosine, respectively; R refers to purine (adenine or guanine); Y refers to pyrimidine (thymine or cytosine); W refers to adenine or thymine; S refers to guanine or cytosine; M refers to adenine or cytosine; K refers to guanine or thymine; H refers to adenine or thymine or cytosine; B refers to guanine or cytosine or thymine; V refers to guanine or adenine or cytosine; D refers to guanine or adenine or thymine; N refers to guanine or adenine or thymine or cytosine.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

The term "nucleic acid fragment" will be understood to mean a nucleotide sequence of reduced length relative to a reference nucleic acid or nucleotide sequence and comprising, consisting essentially of and/or consisting of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of and/or consist of, oligonucleotides having a length of at least about 6, 7, 8, 9, 10, 11, 12, 13, 14, 15, 16, 17, 18, 19, 20, 21, 22, 23, 24, 25, 50, 75, 100, 150, 200, 250, 300, 350, 400, 450, 500, 750, or 1000 consecutive nucleotides of a nucleic acid or nucleotide sequence according to the invention.

An "isolated nucleic acid" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

The term "isolated" can further refer to a nucleic acid, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose.

In representative embodiments of the invention an "isolated" nucleic acid, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense and/or antisense orientation. Thus, a coding sequence of the present invention may be operably linked to a regulatory sequence, thereby allowing its expression in a cell and/or subject.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins.

As is well known in the art, nucleic acid sequences can have changes in one or more nucleotide bases that results in substitution of one or more amino acids, but which do not affect the functional properties of the polypeptide encoded by the nucleotide sequence. It is therefore understood that the invention encompasses more than the specific exemplary nucleotide or amino acid sequences and includes functional equivalents thereof.

For example, alterations in a gene which result in the production of a chemically equivalent amino acid at a given site, but do not affect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Each of the proposed modifications is well within the routine skill in the art, as is determination of retention of biological activity of the encoded products.

Thus, the invention further provides homologues, as well as methods of obtaining homologues, of the polypeptides and/or fragments of this invention from other organisms included in this invention. As used herein, an amino acid sequence or protein is defined as a homologue of a polypeptide or fragment of the present invention if it shares significant homology or identity to a polypeptide, peptide and/or fragment of the present invention. Significant homology or identity means at least 60%, 65%, 70%, 75%, 80%, 81%, 82%, 83%, 84%, 85%, 86%, 87%, 88%, 89%, 90%, 91%, 92%, 93%, 94%, 96%, 97%, 98%, 99% and/or 100% homology or identity with another amino acid sequence. Specifically, by using the nucleic acids that encode the proteins, peptides and fragments of this invention, as a probe or primer, and techniques such as PCR amplification and colony/plaque hybridization, one skilled in the art can identify homologues of the polypeptides, peptides and/or fragments of this invention in other organisms on the basis of information available in the art.

The term "percent identity," as known in the art, describes a relationship between two or more polypeptide sequences or two or more polynucleotide sequences, as determined by comparing the sequences. In the art, "identity" also means the degree of sequence relatedness between polypeptide or polynucleotide sequences as determined by the match between strings of such sequences. "Identity" and "similarity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

Accordingly, the present invention further provides nucleotide sequences having significant sequence similarity or identity to the nucleotide sequences of the present invention. Significant sequence similarity or identity means at least 70%, 75%, 80%, 81%, 82%, 83%, 84%, 85%, 86%, 87%, 88%, 89%, 90%, 91%, 92%, 93%, 94%, 96%, 97%, 98%, 99% and/or 100% similarity or identity with another nucleotide sequence.

Exemplary methods to determine identity are designed to give the best match between the sequences tested. Methods to determine identity and similarity are codified in publicly available computer programs. Sequence alignments and percent identity calculations can be performed using the Megalign program of the LASERGENE bioinformatics computing suite (DNASTAR Inc., Madison, Wis.). Multiple alignment of the sequences may be performed using the Clustal method of alignment (Higgins and Sharp (1989) CABIOS. 5:151-153) with the default parameters (GAP PENALTY=10, GAP LENGTH PENALTY=10). Exemplary default parameters for pairwise alignments using the Clustal method can be selected: KTUPLE 1, GAP PENALTY=3, WINDOW=5 and DIAGONALS SAVED=5.

The term "sequence analysis software" refers to any computer algorithm or software program that is useful for the analysis of nucleotide and/or amino acid sequences. Sequence analysis software is commercially available or can be independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:03-410 (1990), and DNASTAR (DNASTAR, Inc. 1228 S. Park St. Madison, Wis. 53715 USA). Within the context of this application, it will be understood that where sequence analysis software is used for analysis, the results of the analysis will be based on the "default values" of the program referenced, unless otherwise specified. As used herein "default values" will mean any set of values or parameters, which originally load with the software when first initialized.

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, in one embodiment, sequence identity of sequences shorter than a sequence specifically disclosed herein, will be determined using the number of amino acids in the shorter sequence. In percent identity calculations relative weight is not assigned to various manifestations of sequence variation, such as insertions, deletions, substitutions, etc.

In other embodiments, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

The nucleic acid fragments of the instant invention may be used to isolate cDNAs and genes encoding homologous proteins from the same or different organisms. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain I reaction).

For example, genes encoding other SNARE cleaving proteases, either as cDNAs or genomic DNAs, could be isolated directly by using all or a substantial portion of the nucleic acid fragments of the present invention as DNA hybridization probes to screen libraries from any desired organism employing methodology well known to those skilled in the art. Specific oligonucleotide probes based upon the instant nucleic acid sequences can be designed and synthesized by methods known in the art (See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York). Moreover, the entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding arthropod genes. Alternatively, the second primer sequence may be based upon sequences derived from the cloning vector. For example, the skilled artisan can follow the RACE protocol (Frohman et al. (1988) Proc. Natl. Acad. Sci. USA 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) Proc. Natl. Acad. Sci. USA 86:5673-5677; Loh et al. (1989) Science 243:217-220). Products generated by the 3' and 5' RACE procedures can be combined to generate full-length cDNAs (Frohman and Martin (1989) Techniques 1:165).

A "therapeutic polypeptide" as used herein refers to a polypeptide that can alleviate or reduce symptoms that result from an absence or defect in a protein in a cell or subject. Alternatively, a "therapeutic polypeptide" is a polypeptide that otherwise confers a benefit to a subject, e.g., confers anti-spasmodic effects or an improvement in strabismus.

The term "therapeutically effective amount" or "effective amount," as used herein, refers to that amount of a composition of this invention that imparts a modulating effect, which, for example, can be a beneficial effect, to a subject afflicted with a disorder, disease or cosmetic condition, including improvement in the disease, disorder or cosmetic condition of the subject (e.g., in one or more symptoms), delay or reduction in the progression of the disease, disorder or condition, prevention or delay of the onset of the disease, disorder or condition, and/or change in clinical parameters, disease or disorder, etc., as would be well known in the art. The effective amount will vary with the age, general condition of the subject, the severity of the disease, disorder or condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science and Practice of Pharmacy* (20th ed. 2000)). For example, a therapeutically effective amount or effective amount can refer to the amount of a composition, compound, or agent that improves a disease, disorder or condition in a subject by, for example, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

By the terms "treat," "treating" or "treatment of" (or grammatically equivalent terms) it is meant that the severity of the subject's disease, disorder or cosmetic condition is reduced or at least partially improved or ameliorated and/or that some alleviation, mitigation or decrease in at least one clinical symptom is achieved and/or there is a delay in the progression of the disease, disorder or condition and/or prevention or delay of the onset of a disease, disorder, cosmetic condition, etc., as would be well known in the art." Thus, unless the context indicates otherwise, the terms "treat," "treating" or "treatment of" (or grammatically equivalent terms) refer to both prophylactic and therapeutic regimens.

As used herein, the terms "prevent," "prevents," or "prevention" (and grammatical equivalents thereof) are not meant to imply complete abolition of a disease, disorder or cosmetic condition and encompass any type of prophylactic action that reduces the incidence of the disease, disorder or condition, delays the onset and/or progression of the disease, disorder or condition, and/or reduces the symptoms associated with the disease, disorder or condition.

Regulated secretion requires coordinated vesicular trafficking for all processes including biosynthesis, transport, storage, and discharge (11, 12, 13). Signaling in exocrine secretion produces characteristic phosphorylation patterns of intracellular proteins that represent control mechanisms, but the connections between receptor activation and secretory discharge remain incompletely understood.

Pancreatic exocrine secretory discharge is normally mediated by neurological (cholinergic) and hormonal (peptidergic) controls that operate in parallel (14, 15). Earlier work by the present inventors showed that scorpion venom also initiates pancreatic secretion in vitro (16, 17). Clinical studies report that scorpion venoms induce significant pathology including acute pancreatitis in humans following envenomation (18, 19). Experimental evaluation of cellular effects of scorpion venom and its bioactive components reveals signaling that differs from patterns produced by the natural cholinergic and peptidergic secretagogues (unpublished). Tissues treated with these venom preparations produce linear dose response curves in comparison with cholinergic and peptidergic exocrine pancreatic secretagogues; however, discharge is diminished at levels in excess of optimum secretory doses as we have published (16, 17, 20).

Initial evidence of unique scorpion venom mediated activity on secretory mechanisms stemmed from the assessment of tyrosine phosphorylation of cellular proteins. These data provided the first information that cleavage changes to secretory SNARE proteins could disrupt cellular transport and secretion functions (21, 22).

The present invention is based on the unexpected discovery of metalloproteases isolated from scorpion venom that can cleave SNARE complex proteins. Studies with recombinant proteins demonstrated that the cleavage site for VAMP2 is seven residues from the membrane attachment segment, in the loop between the coiled-coil snare bundle binding region and the transmembrane segment adjacent to its carboxyl terminus. VAMP8 is cleaved at a homologous site. The activity of the protease is dependent on divalent ions, which is in agreement with the zinc-binding motif present in the sequence. Previously, proteolytic cleavage of SNARE family components was known to be associated only with large microbial proteins from the genus *Clostridium* that require intracellular cleavage before release of smaller active proteolytic enzymes (23, 24, 25, 26).

Accordingly, the present invention provides, in one aspect, an isolated polypeptide comprising an amino acid sequence selected from the group consisting of (1) SEQ ID NO:1, (2) SEQ ID NO:2, (3) SEQ ID NO:3, (4) SEQ ID NO:4, (5) SEQ ID NO:5 and SEQ ID NO:6, (6) SEQ ID NO:7 and SEQ ID NO:8, and biologically active fragments thereof.

Thus, some particular aspects of the present invention provide an isolated polypeptide comprising an amino acid sequence of SEQ ID NO:2. In other aspects, the present invention provides an isolated polypeptide comprising an amino acid sequence of SEQ ID NO:5 and an amino acid sequence of SEQ ID NO:6. In still other embodiments, the present invention provides a polypeptide comprising an amino acid sequence of SEQ ID NO:7 and an amino acid sequence of SEQ ID NO:8. Further aspects of the invention provide an isolated polypeptide comprising an biologically active fragment of an amino acid sequence selected from the group consisting of (1) SEQ ID NO:1, (2) SEQ ID NO:2, (3) SEQ ID NO:3, (4) SEQ ID NO:4, (5) SEQ ID NO:5 and SEQ ID NO:6, (6) SEQ ID NO:7 and SEQ ID NO:8.

The isolated polypeptides of the present invention are proteases, more specifically, they are metalloproteases and are designated Antarease I (ANI) (SEQ ID NO:1, SEQ ID NO:5 and SEQ ID NO:6), Antarease II (ANTI) (SEQ ID NO:2), Azantarase I (AZI) (SEQ ID NO:3, SEQ ID NO:7 and SEQ ID NO:8), and Azantarease II (AZII) (SEQ ID NO:4). Antarease I and II are isolated from venom of the South American scorpion *Tityus* serrulatus (TSV), while Azantarease I and II are isolated from the venom of a North American scorpion species, *Centruroides sculpturatus* (CSV). These enzymes are shown herein to have SNARE cleaving activity. This was a surprising finding because previously the only known enzymes to cleave SNARE complex proteins were the clostridial neurotoxins (e.g., *Clostridium botulinum toxin*, *Clostridium tetani* toxin).

The proteases of the present invention differ significantly from the clostridal proteases in both their structure (amino acid sequence) and their cleavage sites within the SNARE complex. In fact, it appears that the proteases of the present invention do not share significant homology with any amino acid sequence found in the current sequence databases.

The present invention further provides an isolated nucleic acid encoding a polypeptide comprising an amino acid sequence selected from the group consisting of (1) SEQ ID NO:1, (2) SEQ ID NO:2, (3) SEQ ID NO:3, (4) SEQ ID NO:4, (5) SEQ ID NO:5 and SEQ. ID NO:6, and (6) SEQ ID NO:7 and SEQ ID NO:8.

Other aspects of the invention provide an isolated nucleic acid encoding a nucleotide sequence selected from the group consisting of: (a) the nucleotide sequence encoding a polypeptide comprising the amino acid sequence of (1) SEQ ID NO:1, (2) SEQ ID NO:2, (3) SEQ ID NO:3, (4) SEQ ID NO:4, (5) SEQ ID NO:5 and SEQ ID NO:6, or (6) SEQ ID NO:7 and SEQ ID NO:8; (b) a nucleotide sequence having at least 85% sequence identity to (a) above; and (c) a nucleotide sequence that differs from the nucleotide sequences of (a) or (b) above due to the degeneracy of the genetic code.

Still other aspects of the invention provide an isolated nucleic acid encoding a nucleotide sequence selected from the group consisting of: (a) the nucleotide sequence encoding a polypeptide comprising the amino acid sequence of (1) SEQ ID NO:1, (2) SEQ ID NO:2, (3) SEQ ID NO:3, (4) SEQ ID NO:4, (5) SEQ ID NO:5 and SEQ ID NO:6, or (6) SEQ ID NO:7 and SEQ ID NO:8; (b) a nucleotide sequence having at least 90% sequence identity to (a) above; and (c) a nucleotide sequence that differs from the nucleotide sequences of (a) or (b) above due to the degeneracy of the genetic code.

Additional aspects of the invention provide an isolated nucleic acid encoding a nucleotide sequence selected from the group consisting of: (a) the nucleotide sequence encoding a polypeptide comprising the amino acid sequence of (1) SEQ ID NO:1, (2) SEQ ID NO:2, (3) SEQ ID NO:3, (4) SEQ ID NO:4, (5) SEQ ID NO:5 and SEQ ID NO:6, or (6) SEQ ID NO:7 and SEQ ID NO:8; (b) a nucleotide sequence having at least 95% sequence identity to (a) above; and (c) a nucleotide sequence that differs from the nucleotide sequences of (a) or (b) above due to the degeneracy of the genetic code.

Further aspects of this invention include an isolated nucleic acid encoding a nucleotide sequence selected from the group consisting of: (a) the nucleotide sequence of SEQ ID NO:9 or SEQ ID NO:10; (b) a nucleotide sequence having at least 85% sequence identity to (a) above; and (c) a nucleotide sequence that differs from the nucleotide sequences of (a) or (b) above due to the degeneracy of the genetic code.

Still further aspects of this invention include an isolated nucleic acid encoding a nucleotide sequence selected from the group consisting of: (a) the nucleotide sequence of SEQ ID NO:9 or SEQ ID NO:10; (b) a nucleotide sequence having at least 90% sequence identity to (a) above; and (c) a nucleotide sequence that differs from the nucleotide sequences of (a) or (b) above due to the degeneracy of the genetic code.

The present invention further provides an isolated nucleic acid encoding a nucleotide sequence selected from the group consisting of: (a) the nucleotide sequence of SEQ ID NO:9 or SEQ ID NO:10; (b) a nucleotide sequence having at least 95% sequence identity to (a) above; and (c) a nucleotide sequence that differs from the nucleotide sequences of (a) or (b) above due to the degeneracy of the genetic code.

Nucleic acids of this invention can comprise a nucleotide sequence that can be identical in sequence to the sequence which is naturally occurring or, due to the well-characterized degeneracy of the nucleic acid code, can include alternative codons that encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained. Additionally, the nucleic acids of this invention can also include a nucleic acid strand that is partially complementary to a part of the nucleic acid sequence or completely complementary across the full length of the nucleic acid sequence. Nucleic acid sequences provided herein are presented herein in the 5' to 3' direction, from left to right and are represented using the standard code for representing the nucleotide characters as set forth in the U.S. sequence rules, 37 CFR §§1.821-1.825 and the World Intellectual Property Organization (WIPO) Standard ST.25.

Accordingly, in some aspects of the present invention, a nucleic acid is provided that encodes a nucleotide sequence having a sequence identity in a range from at least 70% to 100% to a nucleotide sequence of the present invention. Thus, the present invention provides a nucleic acid encoding a nucleotide sequence having a sequence identity of at least 70%, at least 75%, at least 80%, at least 81%, at least 82%, at least 83%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% and/or 100%, and the like, to a nucleotide sequence of the present invention.

Several methods known in the art may be used to produce a polynucleotide and/or vector according to this invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-limiting examples of non-viral vectors include plasmids, liposomes, electrically charged lipids (cytofectins), nucleic acid-protein complexes, and biopolymers. In addition to a nucleic acid of interest, a vector may also comprise one or more regulatory regions, expression control sequences, and/or selectable markers useful in selecting, measuring, and monitoring nucleic acid transfer results (e.g., delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Feigner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Feigner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. In representative embodiments, transfection is directed to particular cell types in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell. A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

In other aspects of the invention, a composition is provided comprising an isolated polypeptide of the present invention in a pharmaceutically acceptable carrier. Another aspect of the invention is a composition comprising an isolated nucleic acid of the invention in a pharmaceutically acceptable carrier.

In some embodiments of the present invention, the compositions of the present invention can be useful in treatment or prevention of diseases and disorders. In other embodiments, the compositions of the invention are useful for treatment or prevention of a cosmetic condition in a subject. In some particular aspects of the present invention a method is provided for treating spasmodic muscles in a subject, said method comprising administering to said subject an effective amount of a composition of the present invention as described herein.

In other embodiments, a composition of the present invention as described herein, can be used to treat diseases or disorders including, without limitation, strabismus (crossed or misaligned eyes), blepharospasm (eyelid spasms), hemifacial spasm (unilateral muscle contractions of the face), headache pain including pain due to a migraine headache, cervical dystonia, primary axillary hyperhidrosis (excessive underarm sweating), palmar hyperhidrosis, prostatic symptoms, asthma, stroke symptoms including but not limited to post stroke spasticity, diabetes, obstructive pulmonary disease, achalasia (esophageal motility disorder), chronic obstructive pulmonary disease (COPD), back pain, cerebral palsy including but not limited to pediatric spastic cerebral palsy, chronic anal fissure, delayed gastric emptying, dysphonia including but not limited to spasmodic dysphonia and/or oromandibular dysphonia, epilepsy, epiphora, esotropia, essential tremor, eye lift, facial myokemia, fibromyalgia, flushing, Grey's syndrome, musculoskeletal pain syndromes, pancreatitis, Parkinson's disease, puborectalis syndrome, rhinitis, sialorrhea, tardive dyskinesia, tennis elbow, Tourette's syndrome, urinary incontinence, vaginismus, writer's cramp, laryngeal dystonia, lingual dystonia, cervical dystonia, focal hand dystonia, blepharospasm, anismus, hemifacial spasm, focal spasticity, spasmodic colitis, neurogenic bladder, limb spasticity, tics, bruxism, dysphagia, lacrimation, excessive salivation, excessive gastrointestinal secretions, as well as other secretory disorders, pain from muscle spasms and the like (see, Cheng et al. *Amer. J. Health-Syst. Pharm.* 63:145-152 (2006) and U.S. Pat. No. 6,908,925).

Thus, in some aspects of the invention, a method of treating and/or preventing a disorder in a subject is provided, comprising administering to the subject an effective amount of a composition of the present invention as described herein, wherein the disorder is selected from the group consisting of strabismus (crossed or misaligned eyes), blepharospasm (eyelid spasms), hemifacial spasm (unilateral muscle contractions of the face), headaches including migraine headaches, cervical dystonia, primary axillary hyperhidrosis (excessive underarm sweating), palmar hyperhidrosis, prostatic symptoms including but not limited to benign prostatic hyperplasia, asthma, stroke symptoms, diabetes, obstructive pulmonary disease, achalasia (esophageal motility disorder), chronic obstructive pulmonary disease (COPD), back pain, cerebral palsy including but not limited to pediatric spastic cerebral palsy, chronic anal fissure, delayed gastric emptying, dysphonia including but not limited to spasmodic dysphonia and/or oromandibular dysphonia, epilepsy, epiphora, esotropia, essential tremor, eye lift, facial myokemia, fibromyalgia, flushing, Grey's syndrome, musculoskeletal pain syndromes, pancreatitis, Parkinson's disease, puborectalis syndrome, rhinitis, sialorrhea, tardive dyskinesia, tennis elbow, Tourette's syndrome, urinary incontinence, vaginismus, writer's cramp, laryngeal dystonia, lingual dystonia, cervical dystonia, focal hand dystonia, blepharospasm, anismus, hemifacial spasm, focal spasticity, spasmodic colitis, neurogenic bladder, limb spasticity, tics, bruxism, dysphagia, lacrimation, excessive salivation, excessive gastrointestinal secretions, as well as other secretory disorders, and pain from muscle spasms.

In other aspects of the invention, the cosmetic conditions for which the compositions of the present invention can be useful include, but are not limited to, the prevention and/or treatment of wrinkles and fine lines in the skin of a subject. Such treatments of the skin of a subject include without limitation the treatment of the face and neck. In some embodiments of the invention, such treatments include, but are not limited to, frown wrinkles, forehead wrinkles, lateral canthal wrinkles ("crow's feet"), brow furrows, nose crease wrinkles, wrinkles around the mouth and ears. In some embodiments of the invention, the treatment includes treatment of the cutaneous skin tissue of the subject, and in other embodiments, the treatment includes treatment of the subcutaneous skin tissue of the subject. Treatments of the skin of the face and neck as described above of minimize of appearance of, for example, frown wrinkles, forehead wrinkles, lateral canthal wrinkles ("crow's feet"), brow furrows, nose crease wrinkles, wrinkles around the mouth and ears, over time (e.g., days, weeks, months, years) as compared to the absence of treatment with the compositions of the present invention.

Thus, in some embodiments, the present invention provides a composition comprising, consisting essentially of and/or consisting of a protein and/or nucleic acid of this invention in a pharmaceutically acceptable carrier and, optionally, further comprising other medicinal agents, pharmaceutical agents, stabilizing agents, buffers, carriers, adjuvants, diluents, etc. In other embodiments, the compositions of the present invention comprise a safe and effective amount of the active agents, and a cosmetically acceptable carrier. The phrase "cosmetically acceptable carrier", as used herein, means any substantially non-toxic carrier suitable for administration to the skin, which has good aesthetic properties, and is compatible with the active agent of the present invention. By "compatible" it is meant that the active agent will remain stable and retain substantial activity therein. The carrier can be in a wide variety of forms, such as sprays, emulsions, mousses, liquids, creams, oils, lotions, ointments, gels and solids.

For injection, the carrier will typically be a liquid. For other methods of administration, the carrier may be either solid or liquid. For inhalation administration, the carrier will be respirable, and will preferably be in solid or liquid particulate form (e.g., powder). Further provided herein is a pharmaceutical composition comprising a protein or active fragment thereof of this invention in a pharmaceutically acceptable carrier. Additional compositions of this invention can include any of the proteins, active fragments and/or nucleic acids of this invention in any combination, in a pharmaceutically acceptable carrier.

"Pharmaceutically acceptable," as used herein, means a material that is not biologically or otherwise undesirable, i.e., the material may be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; latest edition). Exemplary pharmaceutically acceptable carriers for the compositions of this invention include, but are not limited to, sterile pyrogen-free water and sterile pyrogen-free physiological saline solution.

A "subject" of this invention includes any subject that is susceptible to the various diseases, disorders and/or cosmetic conditions described herein. Nonlimiting examples of subjects of this invention include mammals, such as humans, nonhuman primates, domesticated mammals (e.g., dogs, cats, rabbits, guinea pigs, rats), livestock and agricultural mammals (e.g., horses, bovine, pigs, goats). In other embodiments, a subject may additionally be an animal such as a bird or reptile. Thus, in some embodiments, a subject can be any domestic, commercially or clinically valuable animal. Subjects may be male or female and may be any age including neonate, infant, juvenile, adolescent, adult, and geriatric subjects. In particular embodiments, the subject is a human. A human subject of this invention can be of any age, gender, race or ethnic group (e.g., Caucasian (white), Asian, African, black, African American, African European, Hispanic, Mideastern, etc.).

A subject of this invention can be "in need of" the methods of the present invention, e.g., because the subject has, or is believed at risk for, muscle spasms and/or another disease, disorder and/or cosmetic condition including those described herein and/or is a subject that would benefit from the methods of this invention. For example, a subject in need of the methods of this invention can be, but is not limited to, a subject diagnosed with, having or suspected to have, or at risk of having or developing strabismus (crossed eyes).

A further aspect of the invention is a method of administering or delivering a scorpion protease polypeptide of the invention, a fragment thereof, and/or a nucleic acid encoding the same, to a subject of this invention. Administration or delivery to a human subject or an animal in need thereof can be by any means known in the art for administering polypeptides, protein fragments and/or nucleic acids. In some embodiments, a polypeptide, fragment thereof and/or nucleic acid is delivered in a therapeutically effective dose in a pharmaceutically acceptable carrier.

In embodiments in which a nucleic acid of this invention is delivered in a viral vector (e.g., a virus particle), the dosage of virus particles to be administered to a subject will depend upon the mode of administration, the disease or condition to be treated, the individual subject's condition, the particular virus vector, and the nucleic acid to be delivered, and can be determined in a routine manner. Exemplary doses are virus titers of at least about $10^5$, $10^6$, $10^7$, $10^8$, $10^9$, $10^{10}$, $10^{11}$, $10^{12}$, $10^3$, $10^{14}$, $10^{15}$ transducing units or more, preferably about $10^8$-$10^{13}$ transducing units, yet more preferably $10^{12}$ transducing units.

Additional non-limiting exemplary modes of administration of the proteins, nucleic acids and vectors of this invention can include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to facial, neck, skeletal, diaphragm and/or cardiac muscle], intradermal, intrapleural, intracerebral, and intraarticular), topical (e.g., to both skin and mucosal surfaces, including airway surfaces, and transdermal administration, and the like, as well as direct tissue or organ injection (e.g., to liver, skeletal muscle, cardiac muscle, diaphragm muscle or brain). Administration can also be to a tumor (e.g., in or a near a tumor or a lymph node). The most suitable route in any given case will depend on the nature and severity of the condition being treated and on the nature of the particular protein, peptide, fragment, nucleic acid or vector that is being used.

Thus, in some aspects of the invention, depending on the mode of administration that is to be used, the compositions can be in a form including, but not limited to liquid, gel, cream, foam, ointment, aerosol, capsule, fluid, powder, semi-solid formulation (e.g., suppository) and/or the like.

Dosages of the polypeptides and/or active fragments thereof and/or nucleic acids encoding the same, to be administered to a subject will depend upon the mode of administration, the disease or condition to be treated, the individual subject's condition including, but not limited to, age and weight, the particular polypeptide and/or active fragment and/or nucleic acid encoding same, and any other agents being administered to the subject and can be determined in a routine manner according to methods well known in the art. In some embodiments, an exemplary dosage range is from about 0.001 unit to about 10,000 units. In other embodiments, the dosage range can be from about 100 units to about 10,000 units. In still other embodiments, the dosage range can be from about 0.01 unit to about 5000 units. In yet further embodiments, the dosage range can be from about 1 unit to about 5000 units. In some embodiments, the dosage range can be from about 10 units to about 1000 units. In other embodiments, the dosage range can be from about 100 units to about 500 units. In still other embodiments, the dosage range can be from about 20 units to about 100 units. Units are $LD_{50}$ units determined using 20-30 g Swiss-Webster mice (see, e.g., U.S. Pat. No. 7,494,661 and U.S. Pat. No. 7,491,403)

Although examples of routes of administration and dosages are provided, the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., McGraw Hill 14th edition).

In particular embodiments, more than one administration (e.g., two, three, four or more administrations) of the polypeptide, fragment and/or nucleic acid of this invention may be employed to achieve the desired result over a period of various intervals, e.g., daily, weekly, monthly, yearly, etc.

The present invention will now be described with reference to the following examples. It should be appreciated that these examples are for the purpose of illustrating aspects of the present invention, and do not limit the scope of the invention as defined by the claims.

EXAMPLES

Example 1

Materials

Caerulein was a gift from Dr. J. Jamieson, Yale University (New Haven, Conn.). Whole dried *Tityus serrulatus* (Lutz and Mello) scorpion venom was from the Instituto Butantan, Sao Paulo, Brazil. Toxin γ, Fractions ν and λ were prepared as previously described (17). *Centruroides sculpturatus* (Ewing) scorpion venom was the gift of Dr. Dean Watt, Creighton University (Omaha, Nebr.). N-isopropyliodo-acetamide was a gift from Dr. J. Inman, NIH. H4 ProteinChips and the calibration standard molecules for the SELDI-TOF mass spectrometer were purchased from Ciphergen Biosystems Inc. (Fremont, Calif.). α-Cyano-4-hydroxy-cinnamicacid (CHCA), sinapinic acid (SA), iodoacetic acid (IAA), and angiotensin were obtained from Sigma (St. Louis, Mo.). The peptide calibration kit was purchased from Ciphergen. H4 ProteinChips and the calibration standard molecules for the SELDITOF mass spectrometer were purchased from Ciphergen Biosystems Inc. (Fremont, Calif.). α-Cyano-4-hydroxy-cinnamic acid (CHCA), sinapinic acid (SA), iodoacetic acid (IAA), and angiotensin were obtained from Sigma (St. Louis, Mo.). N-isopropyliodo-acetamide was a gift from Dr. J. Inman, NIH.

Animal

Dunkin-Hartley guinea pigs were used for collection of pancreatic lobules for in vitro experiments as described (16). Protocols for animal tissue studies were approved by the East Carolina University Institutional Animal Care and Use Committee.

Example 2

Pancreatic Lobule Experiments

Published protocols were followed for the radiolabeled secretion dose-response assays (16, 17). For Western blots, excised lobules were prepared using the Institutional Animal Care and Use Protocols. Incubations in Krebs Ringer Bicarbonate (KRB) under various conditions and times in vitro were as described (16, 17), but without radioactivity. Lobules were homogenized in 25 mM HEPES buffer, pH 6.8, with protease inhibitors (27), then stored at −20° C. Protein concentration was determined using the bicinchoninic acid (BCA) assay (Pierce Chemical Co., Rockford, Ill.).

Pancreatic lobules were pulsed with $^3$H-leucine for 10 min at 37° C. in KRB, then rinsed. Chase-incubation followed for 3 h, then the lobules were homogenized. TCA-precipitable protein samples were processed for scintillation counting. Average resting secretion in untreated control lobules was 7.1%. (FIG. 1A).

Western blots were prepared for VAMP2 and VAMP8 using lobules incubated in KRB in vitro at 37° C. for 3 hours in optimal stimulatory doses for carbachol (CARB) (10 μM) and caerulein (CAER) (1 nM) and hyperstimulatory Tx γ (secretagogue toxin gamma) dose (100 nM). Following the incubation, the lobules were homogenized. Homogenate samples (20 μg/lane) were subjected to SDS-polyacrylamide gel electrophoresis (PAGE) and then transblotted. (FIGS. 1B, 1C, 1D). For samples in FIGS. 1B, 1C, and 1D, n=4 or 2 experiments with duplicate flasks.

Example 3

Electron Microscopic (EM) Immunocytochemistry

Lobules were diced into about 2 mm pieces and fixed in 0.25% glutaraldehyde (Polysciences, Warrington, Pa.)—4% paraformaldehyde (EMS, Hatfield, Pa.) in 0.1 M sodium cacodylate buffer, pH 7.4, at 4° C. overnight. Embedment was in LR White, a low viscosity acrylic embedding medium, (Polysciences, Warrington, Pa.) with thermal cure. Thin sections of 90 nm were collected on Formvar-coated nickel grids. Nonspecific binding was blocked by pre-treatment in 5% normal goat serum (NGS). Grids were then incubated overnight at 4° C. in polyclonal VAMP2 primary antibody (1:50) (Stressgen, Victoria, BC, Canada). To confirm specific labeling, some grids were incubated as negative controls in PBS/1% NGS without primary antibody. After rinsing with PBS, grids were transferred to 10 nm gold conjugated goat anti-rabbit IgG secondary antibody (1:100) (British Biocell International, Ted Pella, Inc., Redding, Calif.) for 1 h. Grids were stained in 4% aqueous uranyl acetate (EMS, Hatfield, Pa.). Sections were examined in a JEOL 1200EX electron microscope equipped with iTEM digital image acquisition software (Soft Imaging System GmbH, Munster, Germany).

Morphometric image analysis was conducted with iTEM. Results represent two experiments and five immunogold incubations.

Example 4

Isolation of Zymogen Granules and Membranes

Zymogen granules (ZG) and their membranes (ZGM) were prepared according to the method of Meldolesi et al. (28) and stored at −80° C. in protease inhibitor buffer (27). Briefly, ZG were purified from guinea pig pancreas homogenates by differential centrifugation. ZGM were prepared from lysed ZG. Protein concentration was measured with the BCA protein assay.

Example 5

Electrophoresis and Blotting

Pancreatic homogenates, ZG, or ZGM (20-25 μg protein/lane) or recombinant SNARE proteins (10-90 μM) were separated by PAGE on 14% SDS Laemmli gels then electroblotted to PVDF (Polyvinylidene Difluoride) membranes. Visualization of bound conjugate on Western blots was by colorimetric staining. Primary antibodies were: polyclonal VAMP2 (Stressgen, Victoria, BC, Canada), VAMP3 (Abeam, Cambridge, Mass.), VAMP8 (Synaptic Systems, Gottingen, Germany), monoclonal PY20 (BD Transduction Labs, Lexington, Ky.). Secondary antibodies were anti-mouse IgG alkaline phosphatase conjugate and anti-rabbit IgG alkaline phosphatase conjugate (Promega Corp., Madison, Wis.). Transblot membranes were developed with 0.1% Coomassie blue R stain. Both Western blots and transblots were routinely repeated a minimum of three times per experiment. Images shown are representative of these.

Example 6

Gel Filtration

Whole dried scorpion venom (500 mg) was solubilized then applied to a Sephadex G-50 column (Superfine) (2.5× 100 cm) as described (17). Fractions (5 ml) were collected, pooled, and freeze dried.

Example 7

Reverse Phase Chromatography

Reverse phase chromatography was carried out using a Vydac 254TP54 $C_{18}$ column. Elution utilized a linear gradient to 60% acetonitrile with 0.1% trifluoroacetic acid (TFA) and uniform flow rate of 1.0 ml/min. Detection followed absorbance recording at both 280 and 215 nm. Resolved components were collected accordingly.

Example 8

Amino Acid Sequence Analysis

Protein samples were hydrolyzed in evacuated and sealed Pyrex glass tubes with 200 μl 6N HCl with 0.5% phenol heated to 110° C. for 20 h. Hydrolyzed samples were stored at −20° C. until time for analysis when hydrolysis solution was removed in a vacuum centrifuge (Savant SpeedVac, Hicksville, N.Y.). The dried samples were dissolved in sample buffer (0.2 M Sodium citrate, pH 2.2) and then loaded into the injection loop to initiate analysis. Analysis was carried out in a Dionex BioLC Amino Acid Analyzer utilizing a ninhydrin detection system and AI450 instrument control and data management system.

Chromatographic peaks were manually collected and volume was reduced by evaporation in a Savant SpeedVac centrifuge followed by storage at −20° C. The peptide cleavage products of VAMP2 by Fx v metalloprotease, separated by reverse phase chromatography, were transferred to a Beckman peptide disk. These peptides and others isolated from cleavage products of the metalloprotease were sequenced on an ABI Procise Model 492 using the pulsed liquid protocol and PTH-amino acids identified by on-line analysis based on a 10-pmol PTH standard.

Example 9

Surface-Enhanced Laser Desorption/Ionization Time Offlight (SELDI-TOF) Mass Spectrometry The SELDI-TOF mass spectrometer was externally calibrated using the [M+H]$^+$ ion peaks of Arg8-vasopressin at 1084.24 m/z, human ACTH 1-24 at 2933.50 m/z, bovine insulin B chain at 3495.94 m/z, human recombinant insulin at 5807.65 m/z, and hirudin BKHV at 7033.61 m/z. All mass spectra were recorded in the positive-ion mode using a Ciphergen PBS II ProteinChip Array reader, a linear laser desorption/ionization-time of flight mass spectrometer with time-lag focusing (29). Prior to SELDI-TOF MS analysis, 1 μl of matrix (saturated CHCA in 50% aqueous acetonitrile containing 0.1% TFA was added to each feature of ProteinChip surface for the analysis. Raw data were analyzed using the computer software provided by the manufacturer and are reported as average masses.

Example 10

BioInformatics and Molecular Modeling

InsightII (Accelrys, Inc., San Diego, Calif.) and Pymol (Delano Scientific LLC, Palo Alto, Calif.)) was used to extend the molecular structures and homology of coiled-coil SNARE crystallography (1sfc.pdb) to provide a model for VAMP2.

Example 11

SNARE Cloning, Expression, Purification, and Characterization

Plasmids, protein expression, and protein purification for full-length SNAP25A, truncated VAMP2 (1-94 and 1-96; *Rattus norvegicus*) and syntaxin1A (1-263), have been described previously (30-34). The VAMP8 plasmid (1-74; *Rattus norvegicus*) was a kind gift from Dr. Gottfried Mieskes (Max Planck Institute for Biophysical Chemistry). All proteins were expressed individually in *Escherichia coli* BL21 (DE3) in Terrific Broth media as 6-His fusions in the pet28a vector (Novagen, Gibbstown, N.J.) except VAMP2 (1-94), which was from the pGEX-4T vector (G.E. Biosciences), as described (35-37). All 6-His tagged proteins were initially purified via Ni-nitrilotriacetic acid (NTA) agarose (Qiagen, Germantown, Md.) according to manufacturer's instructions using native conditions for the syntaxin and SNAP25 and denaturing protocols for VAMP2 and VAMP8. VAMP2 and VAMPS were extensively dialyzed into native condition buffer (50 mM Phosphate, pH 8.0, 300 mM NaCl, 1 mM DTT) before further use. VAMP2 (1-94) was purified by glutathione Sepharose 4B (Amersham Biosciences, Piscataway, N.J.) according to manufacturer's instructions. Syntaxin and SNAP25 were further purified by anion exchange chromatography on monoQ resin (GE Biosciences, Piscataway, N.J.) in 20 mM Tris-HCl, pH 8.2, with elution in a NaCl gradient. The mutations in VAMP2, changing residues E41 to C41, K85 to A85, R86 to S86 and K87 to A87, were introduced into the VAMP2 plasmid using the Quickchange method (Stratagene, Wilmington, Del.) and were verified by sequencing the gene in the final plasmid. The triple mutant VAMP2 was purified by the same method as the wild type (WT).

Example 12

SNARE Proteolysis

Recombinant SNARE proteins were incubated in PBS, pH 7.4, with 1.0 mM $ZnCl_2$ and 1.0 mM $CaCl_2$ for specified times at 37° C. in a water bath with agitation.

Example 13

SNARE Complex Assembly

The ternary SNARE complex was assembled and purified as described previously (310). Briefly, SNARE complexes were formed by adding SNAP25 to syntaxin followed by the addition of VAMP2 (35-37) in a ratio of 1:2:3 (syntaxin:SNAP25:VAMP2), generating SDS resistant SNARE complexes (38). SNARE complex assembly was carried out in 20 mM Tris-HCl, pH 8.2, 200 mM NaCl (TBS) by first incubating at 42° C. for 1.5 h and then 4° C. for 12 h. For the purpose of additional purification of the assembled complex, the histidine tag was not cleaved from VAMP2 but was removed by thrombin treatment from syntaxin and SNAP25 before assembly. The assembly reaction was rebound to Ni-NTA agarose after the 12 h incubation, extensively washed with TBS to remove excess syntaxin and SNAP25, and eluted in TBS containing 200 mM imidazole. The assembled complex was then rebound to monoQ resin. VAMP2 (1-96) does not bind monoQ under loading conditions so excess VAMP2 flows through. The purified ternary SNARE complex was then eluted in a NaCl gradient.

Example 14

Pancreatic Exocrine Regulated Secretion and SNARE Proteins

The exocrine pancreas has great protein biosynthetic capacity as well as the ability to store large quantities of proteins for regulated secretory discharge upon presentation of the proper secretory agonist. The basic unit of this tissue, the pancreatic acinar cell, produces and stores exocrine proteins in vesicular elements in the trans-Golgi network that become mature zymogen or secretory granules positioned near or at the apical plasmalemma. Docking and fusion events have been shown to utilize the SNARE family of proteins to vectorially transport secretory proteins from endoplasmic reticulum through Golgi processing to apical discharge stages of these relatively large granules (≥0.5 µm) (39).

Experimental protocols were designed to differentially characterize stimulation from scorpion venom secretagogues in comparison with classical cholinergic (carbachol) and peptidergic (caerulein) secretagogues. Tissues treated with these venom preparations produce linear dose response curves similar to carbachol and caerulein only up to a level of venom of 1 µg/ml (FIG. 1A). Protein discharge is diminished at higher levels of venom (16, 20). The TSV plot shown is similar to one previously published (16) and is included only for comparison and reference.

Example 15

Scorpion Venom (TSV) Stimulates Pancreatic Exocrine Secretion and Cleaves VAMP SNARES Experiments were carried out at the optimum dose-response level (1 µg/ml) to produce maximal secretion, and at hyperstimulatory amounts of TSV (*Tityus serrulatus* venom) (5 µg/ml and 50 µg/ml). Both positive stimulated (carbachol and caerulein) and unstimulated controls were included (FIGS. 1B and 1D)).

PY20 Western blots reveal part of the pattern of phosphorylation of tyrosine (Tyr) residues (PY20) of proteins in tissue homogenates of guinea pig pancreatic lobules (incubated for 3 and 4 h at varied concentrations of TSV) (FIG. 1B). Significant bands indicating Tyr phosphorylation in pancreatic homogenates were prominent at 17 kDa in control tissue. Samples that included the lowest concentration (1 µg/ml) of TSV appeared the same as control samples. At the highest venom levels (5 and 50 µg/ml) a different pattern emerged. Appearance of bands at 14 and 12 kDa and the concomitant disappearance of the 17 kDa band coinciding with higher concentrations of TSV indicated proteolysis. Bands from venom treated tissue showed marked decreases as quickly as 5 min, even at 4° C. (FIG. 1C). Crude membrane preparations showed the same patterns but post microsomal supernates did not (not shown). The PY20-positive band of 17 kDa was tentatively identified as Vesicle Associated Membrane Protein (VAMP) because of the apparent molecular weight similarities and membrane association. Samples were probed with anti-VAMP antisera (FIG. 1E) that provided putative identity as VAMP2 (2 Tyr residues) or VAMP3 (1 Tyr residue). FIG. 1D shows that none of the classical secretagogues (carbachol and caerulein) or the venom secretagogue toxin gamma (Tx γ) cause tissue alterations during a 3 h incubation, while TSV cleaves the native v-SNAREs, VAMP2 and VAMPS.

Example 16

Identification of a Proteolytic Fraction in TSV

Isolation of a potential venom protease activity involves systematic purification stages. Using Sephadex G-50 and in vitro incubations with recombinant VAMP2, the proteolytic activity in Fx ν was found in the highest molecular weight fraction. Assays of Fx ν for stimulation of radiolabeled (newly-synthesized) proteins revealed weak secretory activity that is diminished in comparison with TSV (FIG. 1A). This fraction is known to have limited or no animal toxicity. Fx λ that follows chromatographically is the next lower molecular weight fraction and has stronger secretagogue activity (FIG. 1A); however, no proteolytic activity was detectable.

Example 17

Electron Microscopy Shows VAMP2 Destruction

Figure 2:
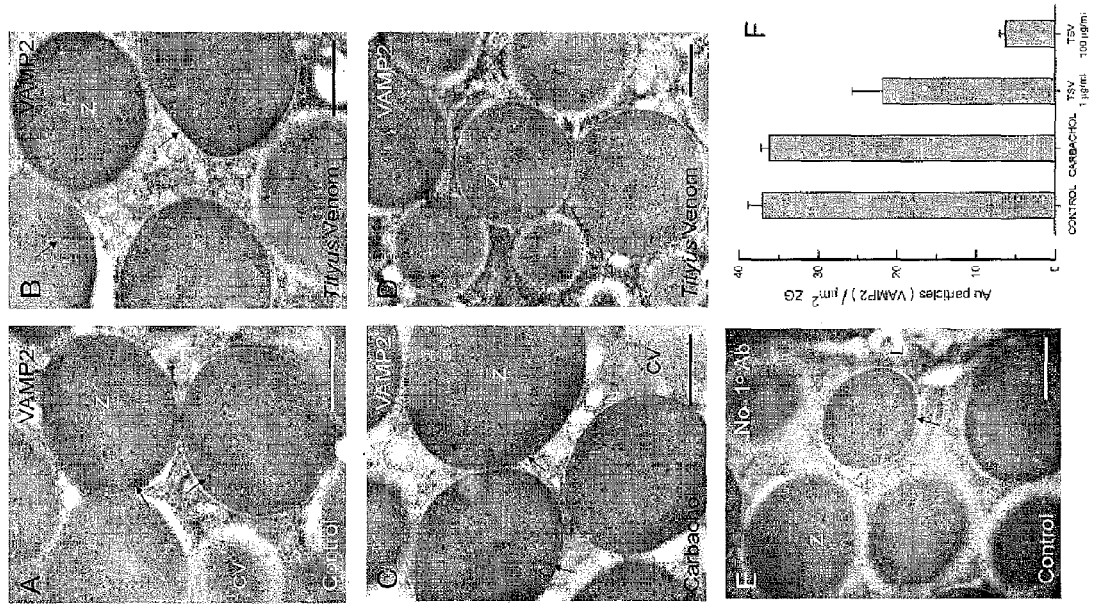
FIGS. 2A-F provide Immunogold VAMP2 electron micrographs. Pancreatic lobules were incubated in vitro for 1 h at 37° C.

Excised guinea pig pancreatic lobules were incubated in vitro with a hyperstimulatory dose of TSV (50 µg/ml) for 1 h at 37° C., rinsed in KRB, then prepared for electron microscopy (EM). Untreated (control) lobules were incubated in KRB alone. Thin sections were probed with primary antisera against VAMP2, then labeled with secondary antibodies conjugated with gold (Au) nanoparticles (10 nm) to detect bound immunoglobulins. Examples of these sections are seen in FIGS. 2A and 2B. Immunocytochemistry of tissues treated in vitro shows decreased colloidal gold labeling in VAMP2, mainly associated with mature ZG, as a result of apparent venom proteolytic activity.

Because the epitope for this antigen in the TSV-treated tissue in FIG. 2B has significantly fewer Au nanoparticles than the control cells (FIG. 2A), the conclusion is that cleavage of VAMP2 has occurred. These EM immunogold studies provide structural verification of the biochemical findings seen in FIG. 1C. A separate experiment extending incubation to 3 h with 100 µg/ml TSV documented the same reduction of VAMP2 Au particles.

Example 18

Figure 3:
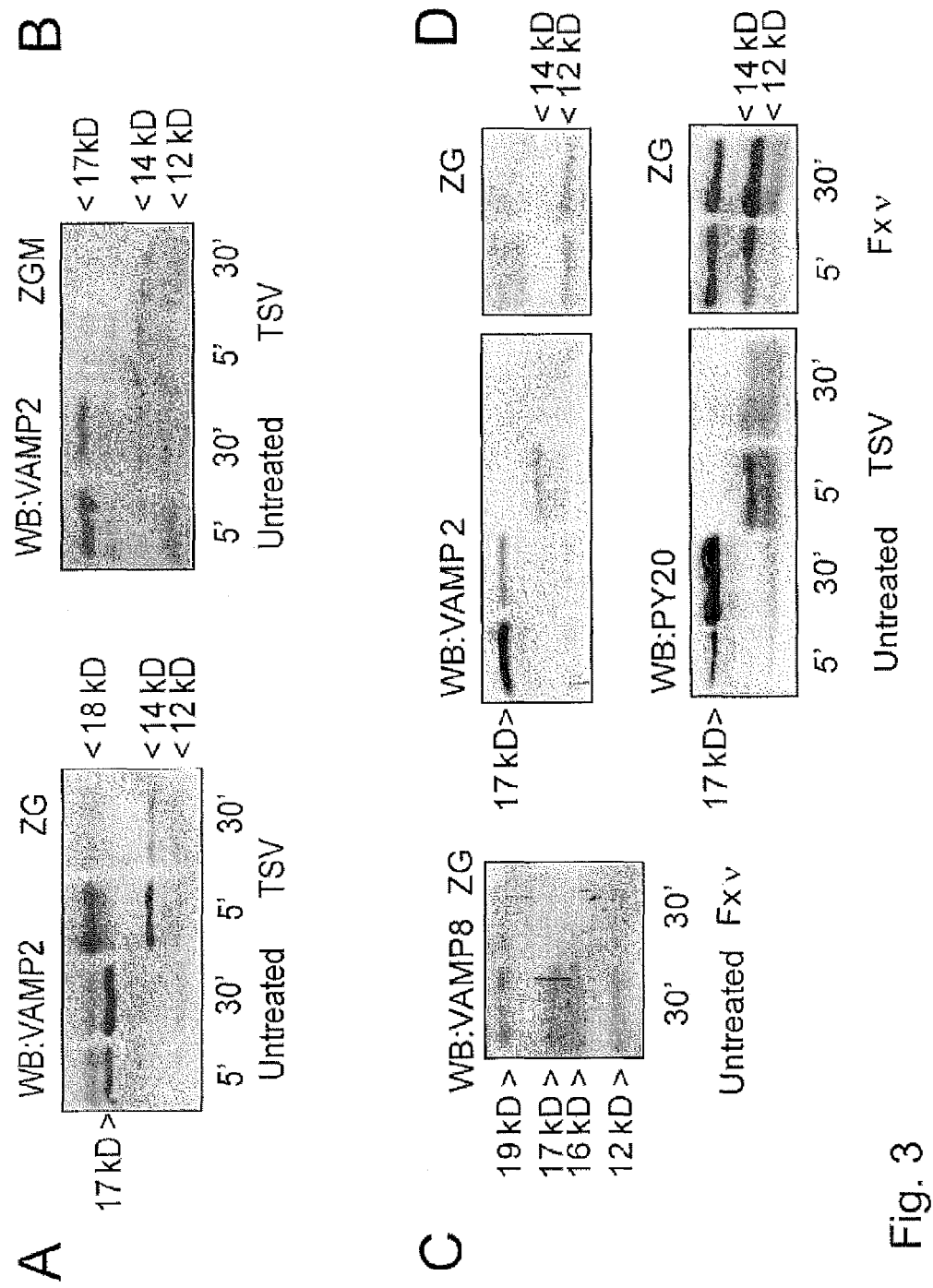
FIGS. 3A-D show cleavage of synaptobrevins by TSV and Fx ν in Zymogen granules (ZG) and zymogen granule membranes (ZGM) in vitro. After in vitro incubation at 37° C., ZG or ZGM (25 µg/lane) were analyzed by SDS-PAGE followed by Western blot.

TSV and Fx ν Degrade VAMP2 and VAMP8 in Isolated Zymogen Granules and Zymogen Granule Membranes Sub-cellular fractionation was carried out to distinguish organelles and membrane systems from cytoplasmic proteins. Zymogen granules (ZG) and their isolated membranes (ZGM) provided significantly less protein diversity; however, the alterations produced by exposure to venom in vitro remained constant. As indicated in FIG. 3, isolated ZG developed cleavages similar to those in pancreatic lobules. TSV produced cleavages in VAMP2 in both ZG (FIG. 3A) and ZGM (FIG. 3B). As seen in FIG. 3C, VAMP8 is also a proteolytic target in ZG during incubation with Fx ν. FIG. 3D shows that whole TSV or Fx ν rapidly cleave VAMP2 (upper panel) even in short incubation periods (5 and 30 min). The PY20 immunoblots (lower panel) parallel this result and are probably reflective of VAMP2 because VAMP8 has no tyrosine residues (see FIG. 6). Carbachol, caerulein and Tx γ do not cause cleavage of VAMP2 in ZG and these patterns are the same as the control in Western blots.

By limiting the source of cellular proteins to the ZG and ZGM, the range of potential cleavage targets was further limited. ZGM include small amounts of VAMP2, known to have a blocked (acetyl) N-terminus, as well as VAMP8 and other similar sized proteins (40). The cleavages produced using these substrates were not sufficient to provide a definition for the site of attack. Interference from integral ZGM proteins and retained cytoplasmic and zymogen proteins prevented assignment of a precise cleavage site with in vitro experiments using tissue sub-fractions. Based upon apparent localization and molecular weight, a source of pure cytoplasmic protein substrate, recombinant VAMP2, was investigated.

Example 19

Recombinant VAMP2 Provides Proteolytic Target Identification

Figure 4:
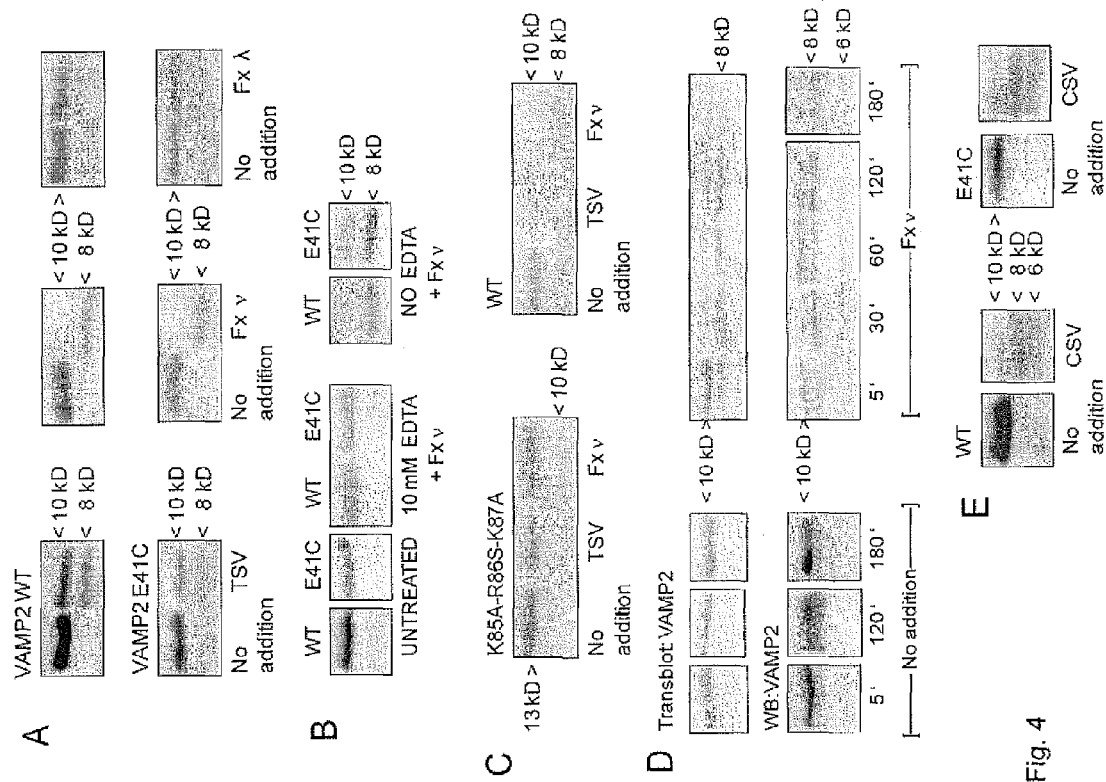
FIGS. 4A-E show the characterization of TSV and Fx ν cleavage of recombinant synaptobrevins via transblots.

To confirm substrate identity and reveal cleavage site both whole venom and chromatographically purified venom proteins were employed with a bacterially expressed, recombinant version of the truncated soluble WT VAMP2 (amino acids 1-94) protein as substrate. VAMP2 or a modified VAMP2 (E41C) was incubated with TSV, Fx ν or Fx λ at 37° C. for 30 min. FIG. 4A (left panels) shows that these VAMP2 substrates are cleaved by TSV. The middle and right panels of FIG. 4A show that Fx ν produces VAMP2 cleavage under these conditions but Fx λ causes no proteolysis. FIG. 4D reveals a potential cleavage product band, differing from the substrate protein by approximately 2 kDa, that appears after 5 min incubation with Fx ν, then becomes more prominent until 120 min, and is evident only faintly at 180 min. Substrate bands diminish at all time points with the exception of the undigested control samples that retain original density. Results presented in FIG. 4D include both transblots as well as Western blots probed for VAMP2. Bands shown in the transblots and Western blots reveal similar outcomes. In addition, the immunoblots visualize another band at 6 kDa. Similar results were observed with the 1-96 fragment of VAMP2. Venom from another New World scorpion, Centruroides sculpturatus, was tested and its proteolytic activity with VAMP2 substrate is shown in FIG. 4E.

Example 20

Fx ν Proteolysis of VAMP2 Requires Divalent Cations

Primary structure determinations of the isolated venom proteases reveal a putative divalent cation binding site. The sequence (HESVHLLGSPHD; SEQ ID NO: 7) that is identified is a recognized motif for zinc binding (41). With this information, experiments were designed to examine the effects of divalent cation chelation on the protease activity of the enzymes.

Fx ν was pre-incubated with 10 mM EDTA for 60 min prior to addition of 10 µM WT VAMP2 (1-94) or VAMP2 variant (E41C) substrate. This chelation step was sufficient to prevent detectable VAMP2 cleavage by Fx ν after 60 min at 37° C. as shown in FIG. 4B. Thus, these experiments further confirm the metalloprotease nature of the Fx ν proteases of the present invention.

Example 21

Amino Acid Substitutions at the VAMP2 Cleavage Site Prevent Proteolysis

Figure 5:
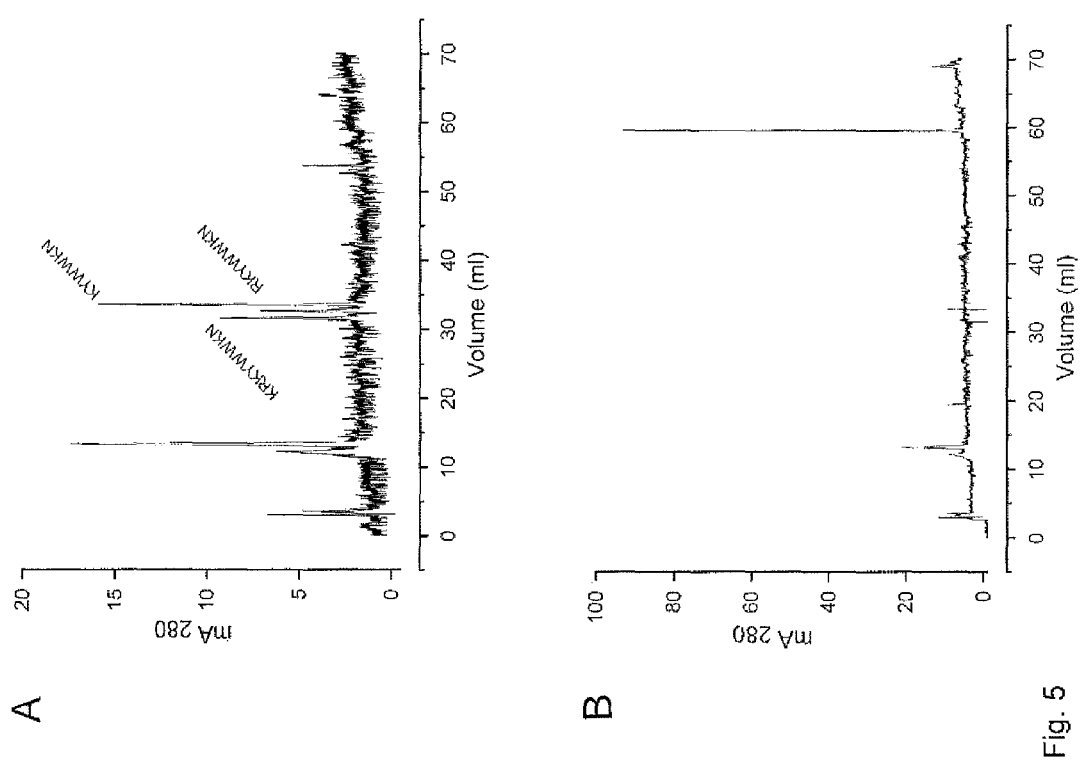
FIGS. 5A-B show the isolation of cleaved VAMP2 peptides using C$_{18}$ reverse phase chromatographic separation of WT 10 µM VAMP2 (1-94) peptides after in vitro incubation at 37° C. for 30 min.
Figure 6:
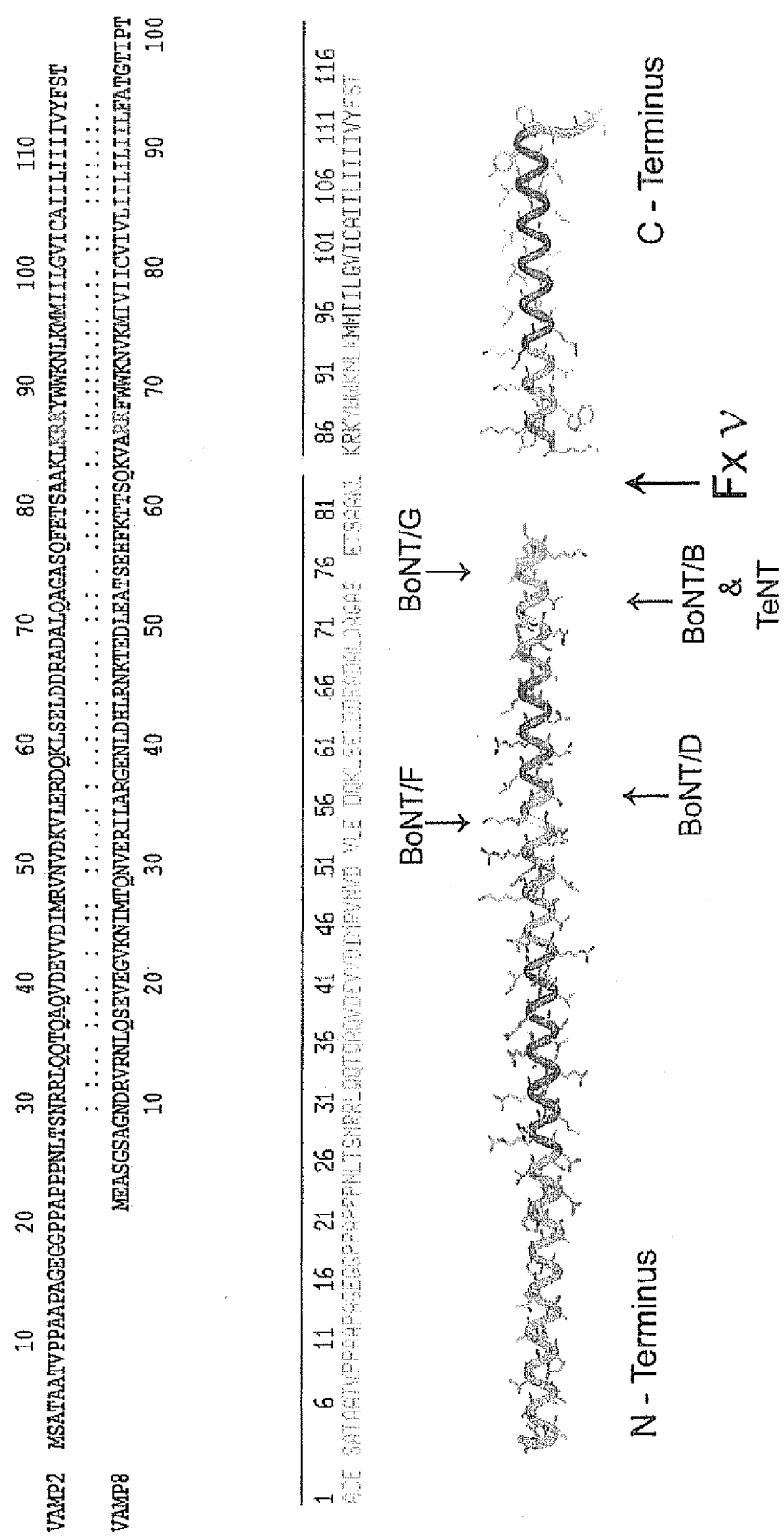
FIG. 6 provides a molecular model of VAMP2 and description of cleavage sites by clostridial toxins and Fx ν. Top: VAMP2 and VAMP8 (rat) FASTA homology alignment with transmembrane segments (95-113). Center: VAMP2 amino acid sequence coordinated with molecular model reflecting sequence features. Bottom: Fx ν cleavage (85, 86, 87) at broken ribbon, BoNT/F (at K52), /D (at R56), /G (at A81) and /B; and TeNT cleavages (F77) and arrows, and SNARE motifs, X1 (A37-R47) and X2 (S61-Q71). Model and FASTA homology generated by InsightII (Accelrys). BoNT (botulinum toxin; /F, /D, /G and /B represent the botulinum toxin serotypes); TeNT (tetanus toxin).

Amino terminal sequencing of VAMP2 reveal that the major proteolytic bands make up the majority of this protein (residues 1-87) and that the smaller cleaved carboxyl terminus is not recovered due to its short sequence (88-94) of seven residues. Reverse phase chromatography of aliquots of the digestion mixtures provided cleaved peptides of both amino and carboxyl termini as determined by protein sequencing (FIG. 5A). Cleavage peptides that were recovered and sequenced indicated enzymatic hydrolysis with new amino termini at residues K85, R86 and K87. These peptides revealed a novel cleavage site within the VAMP2 cytoplasmic portion. Proteolysis on the amino terminal side of K85, R86 and K87 leaves cytoplasmic portions of no more than ten residues or as short as seven residues from the transmembrane segment (FIG. 6). It is clear from the chromatogram in FIG. 5B that VAMP2 incubated as a control in the same experiment remains intact.

A modified version of the cytoplasmic VAMP2 sequence was expressed with an altered amino acid sequence composition replacing the cleavage site. Thus, alanine and serine were substituted for lysine and arginine, respectively, so that the wild type K85 R86 K87, previously determined to be a cleavage site for the Fx ν metalloprotease activity, was altered to A85 S86 A87. Based upon results of both PAGE and reverse phase chromatography ($C_{18}$) these substitutions prevented the previously observed cleavage (FIG. 4C), Amino acid sequence determinations using the ASA85-87 altered cytoplasmic VAMP2 (1-96) following incubation with Fx ν yielded no new amino termini. Based on these data, it is concluded that this protein contains only one site for enzymatic cleavage, K85 R86K87, and substituting A85 S86 A87 for this sequence eliminates Fx ν hydrolysis of cytoplasmic VAMP2.

Example 22

Fx ν also Cleaves VAMP8 and SNAP25

Figure 7:
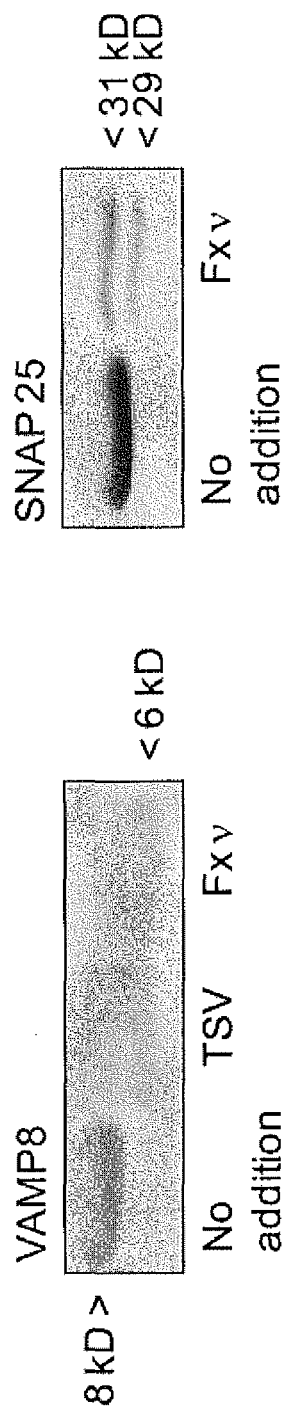
FIG. 7 shows in transblots that TSV and Fx ν cleave other recombinant SNARE proteins. WT 90 µM human endobrevin (VAMP8) cytoplasmic portion 1-74 or WT 20 µM rat SNAP25 full length 1-206 was incubated with either 10 µg/ml TSV or 10 µg/ml Fx ν in vitro at 37° C. for 30 min. Number of experiments: VAMP8, n=3; SNAP25, n=7.

Bacterially expressed, recombinant human VAMPS (1-74) is cleaved upon exposure to Fx ν (FIG. 7). The cleavage site is homologous with that determined for VAMP2. The two cleavage products are at the N-termini of R67 and K68. This cleavage produces 8 (1135.38 Da) and 9 (1291.57 Da) C-terminus residues remaining before the transmembrane segment. These products are confirmed by mass spectrometry. BLASTP aligned sequences are shown in FIG. 6 (top). Similar results are demonstrated in Western blots of treated guinea pig pancreas in vitro (FIG. 1D) and ZG (FIG. 3C). Recombinant WT rat SNAP25 (1-206) is a t-SNARE that is also cleaved by Fx v (FIG. 7). However, it does not include transmembrane segments since it is attached via near-centrally located (palmitoylated) cysteine residues (4—C85, C88, C90, and C92).

Example 23

Assembled SNARE Complex and Fx v

A cleavage site is identified in the recombinant monomeric SNARE component VAMP2 molecules (FIG. 6), which is located at the end of the coiled-coil SNARE motif in VAMP2 (ETSAAKL; (SEQ ID NO:8)) between (L)84 and (K)85; cleavage sites also identified after K85 and R86 and also before K85, R86, and K87.

The potential for proteolysis of assembled coiled-coil SNAREs was examined next

Figure 8:
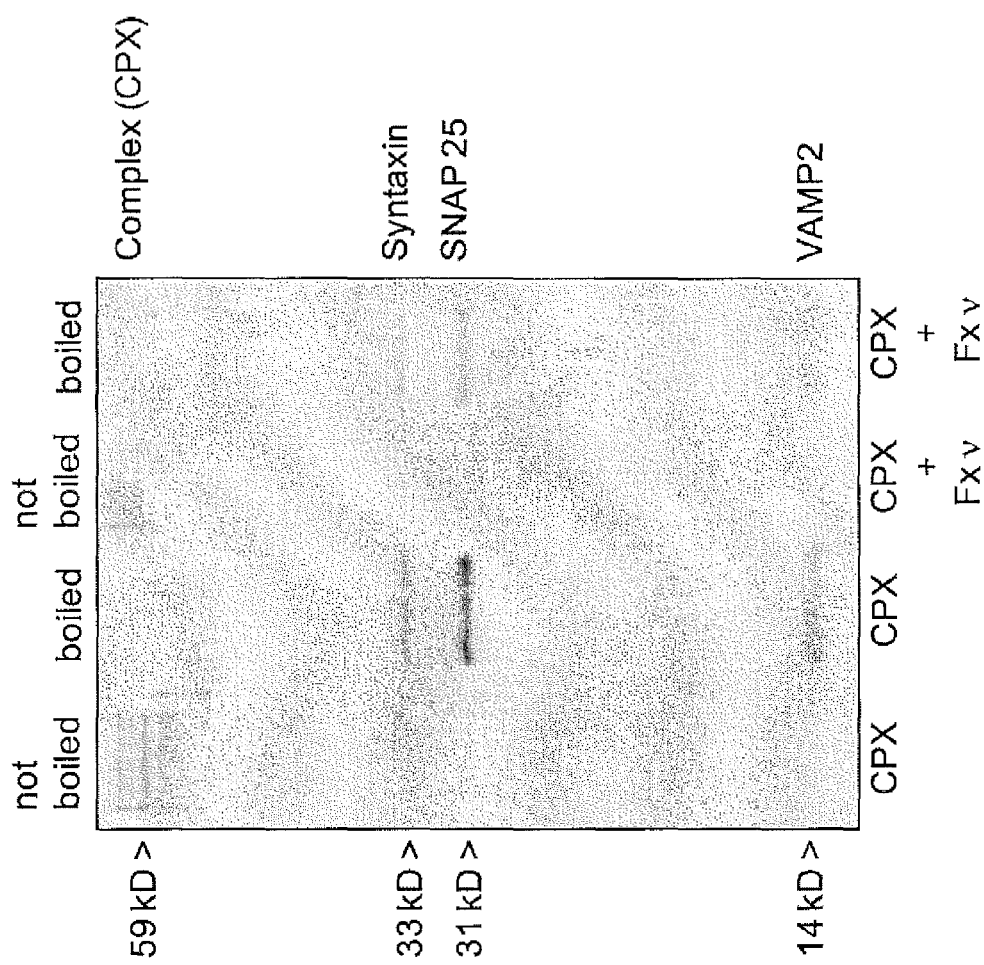
FIG. 8 shows in transblots Fx ν degradation of assembled SNARE complex. SNARE complex (CPX) was incubated with 10 µg/ml Fx ν in vitro at 37° C. for 60 min. After mixing with Laemmli buffer, one sample was loaded onto a gel as intact complex (not boiled) and another sample was disassembled by boiling for 5 min prior to loading (boiled). The image is representative of 14 blots from 3 experiments using 3 sequentially purified SNARE complexes.
Figure 9:
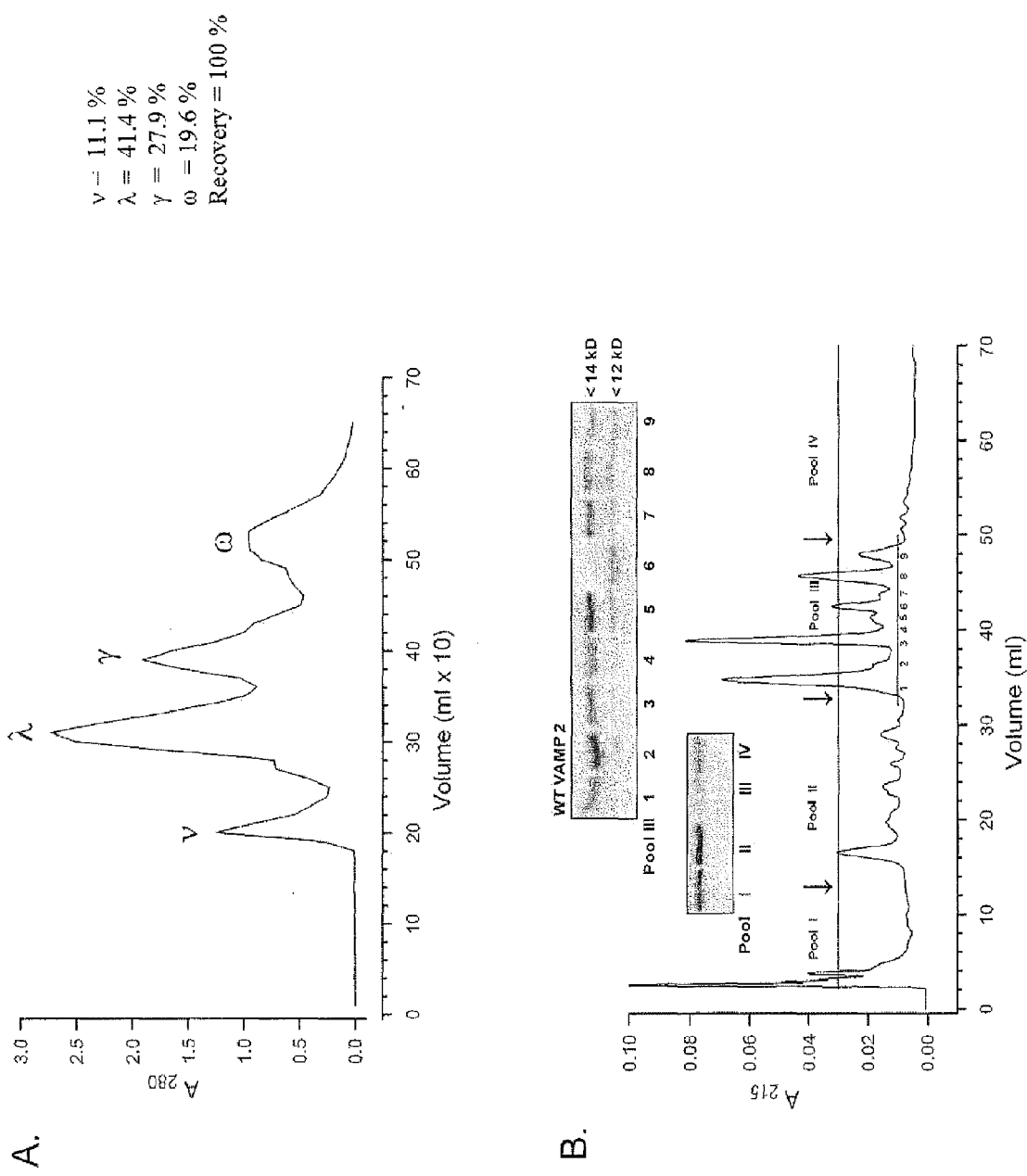
FIG. 9A-B show the chromatographic separation of Fx ν and isolation of Antarease I.

The SNARE component proteins, even those without attached transmembrane segments can be assembled into aligned coiled-coil SNARE structures that share extraordinary characteristics with natural SNARE complexes. These characteristics include stability in 2% SDS, 8M urea solutions, and concurrent heating in excess of 80° C. FIG. 8 demonstrates this unusual stability (Laemmli denaturing gel system—14% acrylamide). Assembled (resistant) SNARE complex (not boiled) as well as disassembled SNARE complex proteins (boiled for 5 min at 100° C.) both without (lanes 1 and 2) and with (lanes 3 and 4; 60 min incubation) exposure to Fx v are subjected to electrophoresis. FIG. 8 shows that in the presence of Fx v there is a clear change in staining density indicating the occurrence of cleavage by Fx v of both the assembled complex (not boiled, lane 3) and the unassembled SNARE complex proteins (boiled, lane 4). Individual SNARE complex components remain as indicated by the presence of residual bands. The visual changes noted are representative of numerous PAGE separations of assembled SNARE complexes that were treated with Fx v.

Example 24

Three, unique and distinct divalent (Zinc) binding sites have been identified that function as the catalytic centers for three of the metalloprotease enzymes of the present invention, which target primary SNARE family proteins as facilitators for intracellular vesicular traffic in eukaryotic cells. These metalloproteases from scorpion venom exhibit previously unknown primary amino acid sequences with characteristic long zinc-binding consensus motif (HExxHxxGxxHD) located near the C-terminal. The zinc binding motifs are set forth below and in FIG. 10.

Antarease I HETAHLIGAPHD

Antarease II HESVHLLGSPHD

Azantarease I HESAHLLGSPHD

The proteolytic function of these enzymes is removed upon chelation of the bound zinc with EDTA, and is restored upon re-addition.

The amino acid sequences of three of the isolated proteases of the present invention for which an amino acid sequence has been determined are set forth in FIG. 10 with the metalloprotease consensus sequence shown in the underlined portion of each sequence.

The amino acid sequence of Antarease II and two reverse translations of this amino acid sequence are shown in FIG. 11.

Example 25

SNARE complex formation is integral to membrane fusion in vesicular trafficking and exocytosis in both neuronal and non-neuronal cells. Effects of clostridial toxins that cleave SNARE proteins in neuronal cells include inhibition of neurotransmitter release (25). In exocrine cells, VAMP2 and VAMP8, described in separate zymogen granule (ZG) populations, may have different roles but share unique participation in transport and exocytotic events (42). VAMP2 is thought to modulate constitutive secretion while VAMP8 has a primary function during regulated secretion (42, 43). An understanding of these functions is fundamental to extending knowledge of transport in normal and diseased cells.

Simultaneous cleavage of multiple SNAREs such as VAMP2, VAMPS and VAMPS would presumably have major physiological consequences since membrane fusion in exocytosis is SNARE dependent in acinar cells (7). Earlier results by the present inventors concerning changes in exocrine pancreatic secretory discharge in hyperstimulation may point to these specific effects. Current studies are examining whether venom-induced VAMP cleavage interferes with pancreatic intracellular transport, exocytosis, and response to secretory signaling. Cleavage of the v-SNAREs, VAMP2 and VAMP8, should result in significant alterations to vesicular transport and similarly would impact secretory mechanisms. Tetanus neurotoxin cleavage of VAMP2 in pancreatic acini has been found to suppress CCK-8 stimulated amylase secretion (44) and VAMPS null mice show a major inhibition of CCK-stimulated regulated pancreatic secretion of amylase while maintaining resting secretion. (43).

EM immunocytochemistry presented herein shows decreased colloidal gold labeling of VAMP2 associated with mature ZG as a result of apparent venom proteolytic activity (FIG. 2). Results define VAMP2 localization to multiple points on the ZGM. Also, Au particles were found on microvesicle-like structures within the ZG content. Following exposure to TSV, few Au particles remain, whether confined to the ZGM or granule content. Enrichment protocols with both isolated ZG and ZGM produced similar cleavage results. In vitro experiments with ZGM provided limited amounts of substrate protein, VAMP2, which has a blocked N-terminus (45), as well as interference from similar sized intracellular proteins. VAMP2 was expressed in *E. coli* to provide substrate confirmation in experiments with chromatographically purified scorpion venom metalloprotease preparations.

Amino acid sequencing of cleaved peptides recovered by chromatography revealed novel cleavage within the cytoplasmic portion of VAMP2. Three consecutive cleavage sites were determined to be 7 residues from the transmembrane segment—closer than Botulinum A (18 res.), G (13 res.) and Tetanus (18 res.) (FIG. 6). Scorpion venom protease activity with potential pathogenic mechanisms has not been described previously. The amino acid sequence (at the amino terminus) of the isolated venom protease is not found in existing amino acid sequence databases. This unique venom protease could be penetrating intact tissue, targeting SNARE proteins that are cleaved within loop segments outside coiled-coil tetrameric SNARE assemblies.

Our studies of the effects of scorpion venom and its bioactive protein components presumed that direct effects were limited to extracellular or plasma membrane components, primarily ion channels (17, 20). Current knowledge of intracellular SNARE cleavage is based upon the metalloprotease toxins from Cl. botulinum and Cl. tetani (23, 26). The principal clostridial toxins produce VAMP cleavages within the region of tetrameric assembly (FIG. 6) (46). Clostridial protease cleavage is also restricted to single microbial serotypes that define single cleavage sites (Id.). The cleavage site presented herein for the scorpion venom metalloprotease is within the loop region immediately following the sequence directly involved in the coiled-coil tetramer and precedes the transmembrane segment that is near the carboxyl terminus (FIG. 6). Depending upon the nature of binding and exposure of the cleavage site, the venom metalloprotease may allow for cleavage of VAMP2 regardless of its presence in an assembled SNARE complex. Findings by other researchers (25) reveal that SNARE tetrameric complex assembly prevents proteolysis by clostridial toxins, thus the venom metalloprotease is further distinguished as a having this unique proteolytic activity.

Enzymes in scorpion venom have not been implicated as primary pathology mediators. The relatively abundant scorpion venom enzyme, hyaluronidase, has been considered the most important enzyme (47). The role for the hyaluronidase activity was thought to be significant only for facilitating tissue penetration and distribution of bioactive venom components in vivo, i.e., as in capture of prey or in human envenomation (48). Morphological studies documented that the in vitro and in vivo effects of TSV and some component protein toxins that produce secretory discharge and tissue alterations are similar to clinical appearances of acute pancreatitis (16, 49). Secretagogues of non-scorpion venom origin used by others can also produce similar effects, but require excessive levels of administration in vivo in order to achieve those results (50).

Pathology has been attributed to the presence in scorpion venom of ion channel mediator activities (51, 52). These neurotoxins are modulators of voltage-gated sodium and potassium channels, chloride channels and calcium channels. There is little correlation between toxin action and physiological effects from stings except that the autonomic nervous system is the primary target (52). Until the description provided in the present application, no scorpion toxins had been associated with intracellular targets.

Intracellular cleavage of the vesicular SNAREs, VAMP2 and VAMPS, in exocrine pancreatic acinar cells is reported in excised tissue incubated in vitro with scorpion venom. Immunocytochemistry using EM located major changes in VAMP2 content in mature ZG following incubation. Studies with isolated ZG and ZGM provide reinforcement for these findings. Definitive results were obtained using bacterially expressed recombinant, cytoplasmic VAMP2. Amino acid sequencing established that the cleavage sites were residues Lysine 85, Arginine 86, and Lysine 87. Replacing these VAMP2 residues with Alanine 85, Serine 86, and Alanine 87 resulted in failure of the venom metalloprotease to cleave the protein. The cleavage sites are not shared with the sites for the only known proteases that target SNARE proteins, the microbial toxins from Cl. botulinum and tetani.

The foregoing is illustrative of the present invention, and is not to be construed as limiting thereof. The invention is defined by the following claims, with equivalents of the claims to be included therein.

REFERENCES

1. Ferro-Novick, S., and Jahn, R. (1994) *Nature* 370, 191-193.
2. Rothman, J. E. (1994) *Nature* 372, 55-63.
3. Sudhof, T. C., (1995) *Nature* 375, 645-653.
4. Jahn, R., and Scheller, R. H. (2006) *Nat. Rev.* 7, 631-643.
5. Breidenbach, M. A., and Brunger, A. T. (2005) *TRENDS in Molecular Medicine* 11, 377-381.
6. Antonin, W., Fasshauer, D., Becker, S., Jahn, R., and Schneider, T. R. (2002) *Nat. Struct. Biol.* 9, 107-111.
7. Hansen, N.J., Antonin, W., and Edwardson, J. M. (1999) *J. Biol. Chem.* 274, 22871-22876.
8. Jahn, R., and Sudhof, T. C. (1999) *Annu. Rev. Biochem.* 68, 863-911.
9. Gaisano, H. Y. (2000) *Pancreas* 20, 217-226.
10. Antonin, W., Wagner, M., Riedel, D., Brose, N., and Jahn, R. (2002) *Mol. Cell. Biol.* 22, 1545-1554.
11. Jena, B. P., Gumkowski, F. D., Konieczko, E. M., Fischer von Mallard, G., Jahn, R., Jamieson, J. D. (1994) *J. Cell Biol* 124, 43-53.
12. Mayer, A. (2002) *Annu. Rev. Cell Dev. Biol.* 18, 289-314.
13. Xu, T., Rammner, B., Margittai, M., Artalejo, A. R., Neher, E., and Jahn, R. (1999) *Cell* 99, 713-722.
14. Palade, G. E. (1975) *Science* 189, 347-358.
15. Scheele, G. A., and Palade, G. E. (1975) *J. Biol. Chem.* 250, 2660-2670.
16. Fletcher Jr., P. L., Fletcher, M. D., and Possani, L. D. (1992) *Eur. J. Cell Biol.* 58, 259-270.
17. Possani, L. D., Martin, B. M., Fletcher, M. D., and Fletcher, Jr., P. L. (1991) *J. Biol, Chem.* 266, 3178-3185.
18. Waterman, J. A. (1938) *Trans. R. Soc. Trop. Med. Hyg.* 31, 607-624.
19. Bartholomew, C. (1970) *Br. Med. J.* 1, 666-668.
20. Fletcher, P. L., Fletcher, M., Fainter, L. K., and Terrian, D. M. (1996) *Toxicon* 34, 1399-1411.
21. Fletcher, P. L., Fletcher, M. D., Weninger, K., Anderson, T. E., and Martin, B. M. (2007) *Mol. Biol. Cell* 18, 272a.
22. Fletcher, P. L., Fletcher, M. D., Weninger, K., Anderson, T. E., and Martin, B. M. (2008) *Mol. Biol. Cell* 19, 1727a.
23. Pellizzari, R., Rossetto, O., Schiavo, G., and Montecucco, C. (1999) *Phil. Trans. R. Soc. Lond. B* 354, 259-268.
24. Schiavo, G., Benfenati, F., Poulain, B., Rossetto, O., Polyerino de Laureto, P., DasGupta, B. R., and Montecucco, C. (1992) *Nature* 359, 832-835.
25. Rossetto, O., Seveso, M., Caccin, P., Schiavo, G., and Montecucco, C. (2001) *Toxicon* 39, 27-41.
26. Schiavo, G., Matteoli, M., and Montecucco, C. (2000) *Physiol. Rev.* 80, 717-766.
27. Valentijn, J. A., Sengupta, D., Gumkowski, F. D., Tang, L. H., Konieczko, E. M. and Jamieson, J. D. (1996) *Eur. J. Cell Biol.* 70, 33-41.
28. Meldolesi, J., Jamieson, J. D., and Palade, G. E. (1971) *J. Cell Biol.* 49, 109-129.
29. Merchant, M., and Weinberger, S. (2000) *Electrophoresis* 21, 1164-1167.
30. Li, Y., Augustine, G. J., and Weninger, K. (2007) *Biophys. J.* 93, 2178-2187.
31. Weninger, K., Bowen, M. E., Chu, S., and Brunger, A. T. (2003) *Proc. Natl. Acad. Sci. USA* 100, 14800-14805.
32. Weninger, K., Bowen, M. E., Chu, S., and Brunger, A. T. (2008) *Structure* 16, 308-320.
33. Bowen, M. E., Weninger, K., Brunger, A. T., and Chu, S. (2004) *Biophys. J.* 87, 3569-3584.
34. Bowen, M. E., Weninger, K., Ernst, J., Chu, S., and Brunger, A. T. (2005) *Biophys. J.* 89, 690-702.
35. Fasshauer, D., Eliason, W. K., Brunger, A. T., and Jahn, R. (1998) *Biochemistry* 37, 10354-10362.
36. Fasshauer, D., Otto, H., Eliason, W. K., Jahn, R., and Brunger, A. T. (1997) *Chem.* 272, 28036-28041.

37. Fasshauer, D., Bruns, D., Shen, B., Jahn, R., and Brunger, A. T. (1997) *J. Biol. Chem.* 272, 4582-4590.
38. Hu, K., Carroll, J., Fedorovich, S., Rickman, C., Sukhodub, A., and Davletov, B. (2002) *Nature* 415, 646-650.
39. Wasle, B., and Edwardson, J. M. (2002) *Cellular Signalling* 14, 191-197.
40. Pickett, J. A., Campos-Toimil, M., Thomas, P., and Edwardson, J. M. (2007) *Biochem. Biophys. Res. Comm.* 359, 599-603.
41. Alberts, I. L., Nadassy, K., and S. J. Wodak (1998) *Protein Sci.* 7, 1700-1716.
42. Weng, N., Thomas, D. D. H., and Groblewski, G. E. (2007) *J. Biol. Chem.* 282, 9635-9645.
43. Wang, C-C., Ng, C. P., Lu, L., Atlashkin, V., Zhang, W., Seet, L-F., and Hong, W. (2004) *Dev. Cell* 7, 359-371.
44. Rosado, J. A., Redondo, P. C., Salida, G. M., Sage, S. O., and Pariente, J. A. (2005) *Am. J. Physiol. Cell Physiol.* 288, 214-221.
45. Sollner, T., Whiteheart, S. W., Brunner, M., Erdjument-Bromage, H., Geromanos, S., Tempst, P., and Rothman, J. E. (1993) *Nature* 362, 318-324.
46. Brunger, A. T., Jin, R., Breidenbach, M. A. (2008) *Cell. Mol. Life. Sci.* 65, 2296-2306.
47. Possani, L. D., Alagon, A. C., Fletcher, P. L. Jr., and Erickson, B. W. (1977) *Arch. Biochem. Biophys.* 180, 394-403.
48. Pessini, A. C., Takao, T. T., Cavalheiro, E. C., Vichnewski, W., Sampaio, S. V., Giglio, J. R., and Arantes, E. C. (2001) *Toxicon* 39, 1495-1504.
49. Fletcher, M. D., Possani, L. D., and Fletcher, P. L. Jr. (1994) *Cell Tissue Res* 278, 255-264.
50. Kloppel, G., Dreyer, T., Willemer, S., Kern, H., Adler, G. (1986) *Virchows Arch [A]* 409, 791-803
51. Gwee, M. C E., Nirthanan, S., Khoo, H., Gopalakrishnakone, P., Kini, R. M., and Cheah, L. (2002) *Clin. and Exp. Pharmacal. and Physiol.* 29, 795-801.
52. Ismail, M. (1995) *Toxicon* 33, 825-858.
53. Cosen-Binker, L. I., Binker, M. G., Wang, C., Hong, W., Gaisano, H. Y. (2008) *J. Clin. Invest.* 118, 2535-2551.

---

That which is claimed is:

1. An isolated polypeptide comprising an amino acid sequence selected from the group consisting of (1) SEQ ID NO:1, (2) SEQ ID NO:2, (3) SEQ ID NO:3, (4) SEQ ID NO:4, (5) a combination of SEQ ID NO:5 and SEQ ID NO:6, and (6) a combination of SEQ ID NO:7 and SEQ ID NO:8, or a biologically active fragment thereof, wherein the isolated polypeptide is a 6-His fusion polypeptide having the activity of proteolytic cleavage of SNAP25, VAMP2 and VAMP8.

2. An isolated nucleic acid encoding a polypeptide comprising an amino acid sequence selected from the group consisting of (1) SEQ ID NO:1, (2) SEQ ID NO:2, (3) SEQ ID NO:3, (4) SEQ ID NO:4, (5) a combination of SEQ ID NO:5 and SEQ ID NO:6, and (6) a combination of SEQ ID NO:7 and SEQ ID NO:8, wherein the encoded polypeptide is a 6-His fusion polypeptide.

3. An isolated nucleic acid encoding a nucleotide sequence selected from the group consisting of:

(a) a nucleotide sequence encoding a polypeptide comprising an amino acid sequence selected from the group consisting of (1) SEQ ID NO:1, (2) SEQ ID NO:2, (3) SEQ ID NO:3, (4) SEQ ID NO:4, (5) a combination of SEQ ID NO:5 and SEQ ID NO:6, and (6) a combination of SEQ ID NO:7 and SEQ ID NO:8, wherein the encoded polypeptide is a 6-His fusion polypeptide;

(b) a nucleotide sequence having at least 85% sequence identity to a nucleotide sequence encoding a polypeptide comprising an amino acid sequence selected from the group consisting of (1) SEQ ID NO:2, (2) SEQ ID NO:4, (3) a combination of SEQ ID NO:5 and SEQ ID NO:6, and (4) a combination of SEQ ID NO:7 and SEQ ID NO:8, wherein the encoded polypeptide is a 6-His fusion polypeptide having the activity of proteolytic cleavage of SNAP25, VAMP2 and VAMP8; and (c) a nucleotide sequence that differs from the nucleotide sequences of (a) or (b) above due to the degeneracy of the genetic code.

4. An isolated nucleic acid encoding a nucleotide sequence selected from the group consisting of:

(a) the nucleotide sequence of SEQ ID NO:9;

(b) a nucleotide sequence having at least 85% sequence identity to (a) above and wherein the encoded polypeptide has the activity of proteolytic cleavage of SNAP25, VAMP2 and VAMP8; and (c) a nucleotide sequence that differs from the nucleotide sequences of (a) or (b) above due to the degeneracy of the genetic code.

5. A composition comprising the isolated polypeptide of claim 1 in a pharmaceutically acceptable carrier.

6. A method of treating muscle spasms in a subject by administering to said subject an effective amount of the composition of claim 5.

7. A method of treating a cosmetic condition in a subject, comprising administering to the subject an effective amount of the composition of claim 5, wherein the cosmetic condition is selected from the group consisting of frown wrinkles, forehead wrinkles, crow's feet, nose crease wrinkles, and any combination thereof.

8. A method of treating a disorder in a subject, comprising administering to the subject an effective amount of the composition of claim 5, wherein the disorder is selected from the group consisting of strabismus, blepharospasm, headaches, cervical dystonia, severe primary axillary hyperhidrosis, prostatic symptoms, asthma, post stroke spasticity diabetes, obstructive pulmonary disease, achalasia, and any combination thereof.

9. A vector comprising an isolated nucleic acid sequence of claim 2.

10. A vector comprising an isolated nucleic acid sequence of claim 3.

11. A vector comprising an isolated nucleic acid sequence of claim 4.

12. The composition of claim 5, wherein the pharmaceutically acceptable carrier comprises sterile pyrogen-free water and/or sterile pyrogen-free physiological saline solution.

13. A composition comprising the isolated polypeptide of claim 1 comprising a cosmetically acceptable carrier.

14. The composition of claim 13, wherein the cosmetically acceptable carrier is in the form of a spray, an emulsion, a mousse, a liquid, a cream, an oil, a lotion, an ointment, a gel or a solid.

15. A method of treating a cosmetic condition in a subject, comprising administering to the subject an effective amount of the composition of claim 13, wherein the cosmetic condition is selected from the group consisting of frown wrinkles, forehead wrinkles, crow's feet, nose crease wrinkles, and any combination thereof.

16. A method of treating a cosmetic condition in a subject, comprising administering to the subject an effective amount of the composition of claim 14, wherein the cosmetic condition is selected from the group consisting of frown wrinkles, forehead wrinkles, crow's feet, nose crease wrinkles, and any combination thereof.

17. A method of expressing the nucleotide sequence of SEQ ID NO:9 in a host cell, comprising:
   introducing into a host cell the nucleotide sequence of SEQ ID NO:9, thereby expressing the nucleotide sequence of SEQ ID NO:9 in a host cell.

18. A method of expressing an isolated nucleic acid sequence of claim 2 in a host cell, comprising:
   introducing into a host cell the isolated nucleic acid sequence of claim 2, thereby expressing the isolated nucleic acid sequence of claim 2 in a host cell.

19. A method of expressing an isolated nucleic acid sequence of claim 3 in a host cell, comprising:
   introducing into a host cell the isolated nucleic acid sequence of claim 3, thereby expressing the isolated nucleic acid sequence of claim 3 in a host cell.

\* \* \* \* \*

SEQUENCE LISTING

<160> NUMBER OF SEQ ID NOS: 10

<210> SEQ ID NO 1
<211> LENGTH: 233
<212> TYPE: PRT
<213> ORGANISM: Tityus serrulatus
<220> FEATURE:
<221> NAME/KEY: MISC_FEATURE
<222> LOCATION: (177)..(191)
<223> OTHER INFORMATION: Xaa is optionally present or absent and can
      be any naturally occurring amino acid

<400> SEQUENCE: 1

Ser Pro Cys Ile Ile Ile Asp Tyr Leu Cys Val Thr Glu Thr Thr Phe
1               5                   10                  15

Thr Glu Arg Phe Lys Thr Asn Lys Glu Leu Leu Glu Tyr Ile Thr Val
            20                  25                  30

Met Phe Thr Gly Val Gln Asn Leu Leu Asp Thr Leu Asn Leu Gly Ile
        35                  40                  45

Lys Ala Gln Val Ile Gly Ile Thr Pro Phe Lys Lys Gln Asn Glu Pro
    50                  55                  60

Ser Phe Ile Glu Asp Ser Ala Ile Pro Gly His Gln Gln Val Leu Asp
65                  70                  75                  80

Pro Val Asp Leu Val Lys Asn Met Ala Lys Tyr Tyr Cys Asn Asn Ala
                85                  90                  95

Lys Gly Leu Ala Lys Asp Ala Asp Ile Ile Met Leu Ile Ser Asn Arg
            100                 105                 110

Lys Leu Gly Glu Leu Gln Asp Asp Gly Thr Val Ala Tyr Asn Thr Ala
        115                 120                 125

Gly Ile Ser Leu Gly Ser Gly Val Cys Lys Gln Cys Ser Lys Val Gly
    130                 135                 140

Val Ala Gln Asp Asp Ser Asp Tyr Asn Glu Arg Val Asp Thr Val Ala
145                 150                 155                 160

His Glu Thr Ala His Leu Ile Gly Ala Pro His Asp Glu Glu Gly Pro
                165                 170                 175

Xaa Xaa Xaa Xaa Xaa Xaa Xaa Xaa Xaa Xaa Xaa Xaa Xaa Xaa Xaa Ser
            180                 185                 190

Asp Gly Tyr Ile Met Gly Ser Gly Asn Asn Lys Val Asn Lys Phe Lys
        195                 200                 205

```
Phe Ser Lys Cys Thr Lys Lys Cys Val Glu His Leu Leu Ser Leu Pro
    210                 215                 220
Arg Ala Ser Cys Val Leu Ala Asp Cys
225                 230
```

<210> SEQ ID NO 2
<211> LENGTH: 236
<212> TYPE: PRT
<213> ORGANISM: Tityus serrulatus

<400> SEQUENCE: 2

```
Asp Asp Asp Cys Ile Val Val Glu Tyr Tyr Ile Val Thr Asp Ser Ala
1               5                   10                  15
Phe Thr Lys Arg Phe Lys Ser Asn Ser Ala Leu Thr Asn Tyr Val Thr
            20                  25                  30
Val Met Phe Thr Gly Val Gln Glu Leu Leu Asp Thr Leu Asn Leu Gly
        35                  40                  45
Ile Gly Val Arg Leu Leu Gly Val Thr Thr Phe Thr Glu Lys Thr Glu
    50                  55                  60
Pro Ser Phe Ile Lys Asp Asn Leu Ile Pro Gly Pro Ala Ala Phe
65                  70                  75                  80
Asp Pro Asp Val Leu Ile Ser Ala Met Ser Lys Tyr Tyr Cys Asn His
                85                  90                  95
Gln Thr Gly Leu Ala Lys Asp Thr Asp Leu Ile Phe Leu Ile Thr Ala
            100                 105                 110
Arg Gly Met Gly Asp Pro Arg Glu Asp Gly Thr Val Asp Ile Asn Thr
        115                 120                 125
Ala Gly Ile Ala Asn Ser Ala Gly Val Cys Lys Pro Cys Phe Lys Ser
    130                 135                 140
Gly Ile Ala Thr Asp Asp Ser Asp Tyr Asn Glu Arg Val Asp Thr Leu
145                 150                 155                 160
Ala His Glu Ser Val His Leu Leu Gly Ser Pro His Asp Gly Glu Gly
                165                 170                 175
Pro Asn Leu Val Ser Leu Gly Ser Pro Gly Ala Ala Asn Cys Pro Ala
            180                 185                 190
Lys Ala Gly Tyr Ile Met Gly Asn Arg Asn Asp Lys Val Asn Lys Tyr
        195                 200                 205
Lys Phe Ser Asn Cys Thr Lys Lys Cys Val Glu Tyr Leu Leu Ser Lys
    210                 215                 220
Pro Thr Ala Ser Cys Ile Phe Gln Gln Cys Ser Asp
225                 230                 235
```

<210> SEQ ID NO 3
<211> LENGTH: 235
<212> TYPE: PRT
<213> ORGANISM: Centruroides sculpturatus
<220> FEATURE:
<221> NAME/KEY: MISC_FEATURE
<222> LOCATION: (179)..(192)
<223> OTHER INFORMATION: Xaa is optionally present or absent and can
      be any naturally occurring amino acid

<400> SEQUENCE: 3

```
Lys Asp Gln Cys Ile Val Val Glu Cys Leu Val Val Thr Glu Ser Ala
1               5                   10                  15
Phe Thr Lys Arg Phe Glu Thr Thr Lys Ala Leu Thr Glu Tyr Val Thr
            20                  25                  30
```

```
Val Met Tyr Thr Gly Val Gln Asn Leu Ile Asp Thr Leu Gln Leu Gly
        35                  40                  45

Ile Lys Phe Arg Leu Leu Gly Ile Asp Pro Phe Thr Lys Glu Thr Glu
 50                  55                  60

Pro Pro Tyr Ile Glu Glu Ser Ala Asn Pro Val Asn Pro Lys Tyr Leu
 65                  70                  75                  80

Asn Pro Leu Asp Leu Ile Asp Arg Met Gly Lys Tyr Tyr Cys Asn His
                 85                  90                  95

Ala Thr Gly Leu Ala Lys Asp Ala Asp Met Ile Met Leu Leu Val Thr
            100                 105                 110

Arg Asn Leu Gly Glu Leu Lys Asp Asp Gly Thr Val Lys Phe Arg Val
            115                 120                 125

Val Gly Leu Ala Tyr Lys Gly Ala Val Cys Lys Gln Cys Tyr Lys Val
130                 135                 140

Gly Val Cys Lys Asp Asp Ser Tyr Tyr Asn Glu Arg Val Asp Thr Val
145                 150                 155                 160

Ala His Glu Ser Ala His Leu Leu Gly Ser Pro His Asp Gly Glu Pro
                165                 170                 175

Gly Ala Xaa Xaa Xaa Xaa Xaa Xaa Xaa Xaa Xaa Xaa Xaa Xaa Xaa Xaa
            180                 185                 190

Lys Asp Gly Tyr Ile Met Gly Asn Arg Arg Asp Lys Val Asn Lys Tyr
            195                 200                 205

Lys Phe Ser Lys Cys Thr Lys Lys Cys Val Lys Asp Ala Leu Ser Leu
            210                 215                 220

Pro Glu Ala Lys Cys Val Tyr Glu Ser Cys Gly
225                 230                 235

<210> SEQ ID NO 4
<211> LENGTH: 20
<212> TYPE: PRT
<213> ORGANISM: Centruroides sculpturatus

<400> SEQUENCE: 4

Ser Gly Lys Cys Ile Ile Val Asp Cys Leu Val Leu Thr Glu Asn Ala
 1               5                  10                  15

Phe Thr Lys Arg
            20

<210> SEQ ID NO 5
<211> LENGTH: 176
<212> TYPE: PRT
<213> ORGANISM: Tityus serrulatus

<400> SEQUENCE: 5

Ser Pro Cys Ile Ile Ile Asp Tyr Leu Cys Val Thr Glu Thr Thr Phe
 1               5                  10                  15

Thr Glu Arg Phe Lys Thr Asn Lys Glu Leu Leu Glu Tyr Ile Thr Val
                 20                  25                  30

Met Phe Thr Gly Val Gln Asn Leu Leu Asp Thr Leu Asn Leu Gly Ile
            35                  40                  45

Lys Ala Gln Val Ile Gly Ile Thr Pro Phe Lys Gln Asn Glu Pro
 50                  55                  60

Ser Phe Ile Glu Asp Ser Ala Ile Pro Gly His Gln Gln Val Leu Asp
 65                  70                  75                  80

Pro Val Asp Leu Val Lys Asn Met Ala Lys Tyr Tyr Cys Asn Asn Ala
                 85                  90                  95
```

```
Lys Gly Leu Ala Lys Asp Ala Asp Ile Ile Met Leu Ile Ser Asn Arg
            100                 105                 110

Lys Leu Gly Glu Leu Gln Asp Asp Gly Thr Val Ala Tyr Asn Thr Ala
            115                 120                 125

Gly Ile Ser Leu Gly Ser Gly Val Cys Lys Gln Cys Ser Lys Val Gly
            130                 135                 140

Val Ala Gln Asp Asp Ser Asp Tyr Asn Glu Arg Val Asp Thr Val Ala
145                 150                 155                 160

His Glu Thr Ala His Leu Ile Gly Ala Pro His Asp Glu Glu Gly Pro
                165                 170                 175
```

<210> SEQ ID NO 6
<211> LENGTH: 42
<212> TYPE: PRT
<213> ORGANISM: Tityus serrulatus

<400> SEQUENCE: 6

```
Ser Asp Gly Tyr Ile Met Gly Ser Gly Asn Asn Lys Val Asn Lys Phe
1               5                   10                  15

Lys Phe Ser Lys Cys Thr Lys Lys Cys Val Glu His Leu Leu Ser Leu
            20                  25                  30

Pro Arg Ala Ser Cys Val Leu Ala Asp Cys
            35                  40
```

<210> SEQ ID NO 7
<211> LENGTH: 178
<212> TYPE: PRT
<213> ORGANISM: Centruroides sculpturatus

<400> SEQUENCE: 7

```
Lys Asp Gln Cys Ile Val Val Glu Cys Leu Val Val Thr Glu Ser Ala
1               5                   10                  15

Phe Thr Lys Arg Phe Glu Thr Thr Lys Ala Leu Thr Glu Tyr Val Thr
            20                  25                  30

Val Met Tyr Thr Gly Val Gln Asn Leu Ile Asp Thr Leu Gln Leu Gly
            35                  40                  45

Ile Lys Phe Arg Leu Leu Gly Ile Asp Pro Phe Thr Lys Glu Thr Glu
        50                  55                  60

Pro Pro Tyr Ile Glu Glu Ser Ala Asn Pro Val Asn Pro Lys Tyr Leu
65                  70                  75                  80

Asn Pro Leu Asp Leu Ile Asp Arg Met Gly Lys Tyr Tyr Cys Asn His
            85                  90                  95

Ala Thr Gly Leu Ala Lys Asp Ala Asp Met Ile Met Leu Leu Val Thr
            100                 105                 110

Arg Asn Leu Gly Glu Leu Lys Asp Asp Gly Thr Val Lys Phe Arg Val
            115                 120                 125

Val Gly Leu Ala Tyr Lys Gly Ala Val Cys Lys Gln Cys Tyr Lys Val
            130                 135                 140

Gly Val Cys Lys Asp Asp Ser Tyr Tyr Asn Glu Arg Val Asp Thr Val
145                 150                 155                 160

Ala His Glu Ser Ala His Leu Leu Gly Ser Pro His Asp Gly Glu Pro
                165                 170                 175

Gly Ala
```

<210> SEQ ID NO 8
<211> LENGTH: 43
<212> TYPE: PRT

<213> ORGANISM: Centruroides sculpturatus

<400> SEQUENCE: 8

Lys Asp Gly Tyr Ile Met Gly Asn Arg Arg Asp Lys Val Asn Lys Tyr
1               5                   10                  15

Lys Phe Ser Lys Cys Thr Lys Lys Cys Val Lys Asp Ala Leu Ser Leu
            20                  25                  30

Pro Glu Ala Lys Cys Val Tyr Glu Ser Cys Gly
        35                  40

<210> SEQ ID NO 9
<211> LENGTH: 708
<212> TYPE: DNA
<213> ORGANISM: Artificial
<220> FEATURE:
<223> OTHER INFORMATION: Reverse translation of SEQ ID NO:2

<400> SEQUENCE: 9
gatgatgatt gcattgtggt ggaatattat attgtgaccg atagcgcgtt taccaaacgc      60
tttaaaagca acagcgcgct gaccaactat gtgaccgtga tgtttaccgg cgtgcaggaa    120
ctgctggata ccctgaacct gggcattggc gtgcgcctgc tgggcgtgac cacctttacc    180
gaaaaaaccg aaccgagctt tattaaagat aacctgattc cgggcccgcc ggcggcgttt    240
gatccggatg tgctgattag cgcgatgagc aaatattatt gcaaccatca gaccggcctg    300
gcgaaagata ccgatctgat ttttctgatt accgcgcgcg gcatgggcga tccgcgcgaa    360
gatggcaccg tggatattaa caccgcgggc attgcgaaca gcgcgggcgt gtgcaaaccg    420
tgctttaaaa gcggcattgc gaccgatgat agcgattata cgaacgcgt ggatacctg    480
gcgcatgaaa gcgtgcatct gctgggcagc ccgcatgatg gcgaaggccc gaacctggtg    540
agcctgggca gcccgggcgc ggcgaactgc ccggcgaaag cgggctatat tatgggcaac    600
cgcaacgata aagtgaacaa atataaatt agcaactgca ccaaaaaatg cgtggaatat    660
ctgctgagca aaccgaccgc gagctgcatt tttcagcagt gcagcgat              708

<210> SEQ ID NO 10
<211> LENGTH: 708
<212> TYPE: DNA
<213> ORGANISM: Artificial
<220> FEATURE:
<223> OTHER INFORMATION: Reverse translation of SEQ ID NO:2
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (45)..(45)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:

```
<221> NAME/KEY: misc_feature
<222> LOCATION: (54)..(54)
<223> OTHER INFORMATION: n is a, c, g, t or u
<220> FEATURE:
<221> NAME/KEY: misc_feature
<222> LOCATION: (60)..(60)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (75)..(75)
<223> OTHER INFORMATION: n is a, c, g, t or u
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (81)..(81)
<223> OTHER INFORMATION: n is a, c, g, t or u
<220> FEATURE:
<221> NAME/KEY: misc_feature
<222> LOCATION: (84)..(84)
<223> OTHER INFORMATION: n is a, c, g, t or u
<220> FEATURE:
<221> NAME/KEY: misc_feature
<222> LOCATION: (93)..(93)
<223> OTHER INFORMATION: n is a, c, g, t or u
<220> FEATURE:
<221> NAME/KEY: misc_feature
<222> LOCATION: (96)..(96)
<223> OTHER INFORMATION: n is a, c, g, t or u
<220> FEATURE:
<221> NAME/KEY: misc_feature
<222> LOCATION: (99)..(99)
<223> OTHER INFORMATION: n is a, c, g, t or u
<220> FEATURE:
<221> NAME/KEY: misc_feature
<222> LOCATION: (108)..(108)
<223> OTHER INFORMATION: n is a, c, g, t or u
<220> FEATURE:
<221> NAME/KEY: misc_feature
<222> LOCATION: (111)..(111)
<223> OTHER INFORMATION: n is a, c, g, t or u
<220> FEATURE:
<221> NAME/KEY: misc_feature
<222> LOCATION: (114)..(114)
<223> OTHER INFORMATION: n is a, c, g, t or u
<220> FEATURE:
<221> NAME/KEY: misc_feature
<222> LOCATION: (123)..(123)
<223> OTHER INFORMATION: n is a, c, g, t or u
<220> FEATURE:
<221> NAME/KEY: misc_feature
<222> LOCATION: (126)..(126)
<223> OTHER INFORMATION: n is a, c, g, t or u
<220> FEATURE:
<221> NAME/KEY: misc_feature
<222> LOCATION: (132)..(132)
<223> OTHER INFORMATION: n is a, c, g, t or u
<220> FEATURE:
<221> NAME/KEY: misc_feature
<222> LOCATION: (135)..(135)
<223> OTHER INFORMATION: n is a, c, g, t or u
<220> FEATURE:
<221> NAME/KEY: misc_feature
<222> LOCATION: (141)..(141)
<223> OTHER INFORMATION: n is a, c, g, t or u
<220> FEATURE:
<221> NAME/KEY: misc_feature
<222> LOCATION: (144)..(144)
<223> OTHER INFORMATION: n is a, c, g, t or u
<220> FEATURE:
<221> NAME/KEY: misc_feature
<222> LOCATION: (150)..(150)
<223> OTHER INFORMATION: n is a, c, g, t or u
```

-continued

```
<220> FEATURE:
<221> NAME/KEY: misc_feature
<222> LOCATION: (153)..(153)
<223> OTHER INFORMATION: n is a, c, g, t or u
<220> FEATURE:
<221> NAME/KEY: misc_feature
<222> LOCATION: (156)..(156)
<223> OTHER INFORMATION: n is a, c, g, t or u
<220> FEATURE:
<221> NAME/KEY: misc_feature
<222> LOCATION: (159)..(159)
<223> OTHER INFORMATION: n is a, c, g, t or u
<220> FEATURE:
<221> NAME/KEY: misc_feature
<222> LOCATION: (162)..(162)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (168)..(168)
<223> OTHER INFORMATION: n is a, c, g, t or u
<220> FEATURE:
<221> NAME/KEY: misc_feature
<222> LOCATION: (171)..(171)
<223> OTHER INFORMATION: n is a, c, g, t or u
<220> FEATURE:
<221> NAME/KEY: misc_feature
<222> LOCATION: (174)..(174)
<223> OTHER INFORMATION: n is a, c, g, t or u
<220> FEATURE:
<221> NAME/KEY: misc_feature
<222> LOCATION: (180)..(180)
<223> OTHER INFORMATION: n is a, c, g, t or u
<220> FEATURE:
<221> NAME/KEY: misc_feature
<222> LOCATION: (189)..(189)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (198)..(198)
<223> OTHER INFORMATION: n is a, c, g, t or u
<220> FEATURE:
<221> NAME/KEY: misc_feature
<222> LOCATION: (216)..(216)
<223> OTHER INFORMATION: n is a, c, g, t or u
<220> FEATURE:
<221> NAME/KEY: misc_feature
<222> LOCATION: (222)..(222)
<223> OTHER INFORMATION: n is a, c, g, t or u
<220> FEATURE:
<221> NAME/KEY: misc_feature
<222> LOCATION: (225)..(225)
<223> OTHER INFORMATION: n is a, c, g, t or u
<220> FEATURE:
<221> NAME/KEY: misc_feature
<222> LOCATION: (228)..(228)
<223> OTHER INFORMATION: n is a, c, g, t or u
<220> FEATURE:
<221> NAME/KEY: misc_feature
<222> LOCATION: (231)..(231)
<223> OTHER INFORMATION: n is a, c, g, t or u
<220> FEATURE:
<221> NAME/KEY: misc_feature
<222> LOCATION: (234)..(234)
<223> OTHER INFORMATION: n is a, c, g, t or u
<220> FEATURE:
<221> NAME/KEY: misc_feature
<222> LOCATION: (237)..(237)
<223> OTHER INFORMATION: n is a, c, g, t or u
<220> FEATURE:
<221> NAME/KEY: misc_feature
<222> LOCATION: (246)..(246)
```

-continued

```
<223> OTHER INFORMATION: n is a, c, g, t or u
<220> FEATURE:
<221> NAME/KEY: misc_feature
<222> LOCATION: (252)..(252)
<223> OTHER INFORMATION: n is a, c, g, t or u
<220> FEATURE:
<221> NAME/KEY: misc_feature
<222> LOCATION: (255)..(255)
<223> OTHER INFORMATION: n is a, c, g, t or u
<220> FEATURE:
<221> NAME/KEY: misc_feature
<222> LOCATION: (261)..(261)
<223> OTHER INFORMATION: n is a, c, g, t or u
<220> FEATURE:
<221> NAME/KEY: misc_feature
<222> LOCATION: (264)..(264)
<223> OTHER INFORMATION: n is a, c, g, t or u
<220> FEATURE:
<221> NAME/KEY: misc_feature
<222> LOCATION: (270)..(270)
<223> OTHER INFORMATION: n is a, c, g, t or u
<220> FEATURE:
<221> NAME/KEY: misc_feature
<222> LOCATION: (294)..(294)
<223> OTHER INFORMATION: n is a, c, g, t or u
<220> FEATURE:
<221> NAME/KEY: misc_feature
<222> LOCATION: (297)..(297)
<223> OTHER INFORMATION: n is a, c, g, t or u
<220> FEATURE:
<221> NAME/KEY: misc_feature
<222> LOCATION: (300)..(300)
<223> OTHER INFORMATION: n is a, c, g, t or u
<220> FEATURE:
<221> NAME/KEY: misc_feature
<222> LOCATION: (303)..(303)
<223> OTHER INFORMATION: n is a, c, g, t or u
<220> FEATURE:
<221> NAME/KEY: misc_feature
<222> LOCATION: (312)..(312)
<223> OTHER INFORMATION: n is a, c, g, t or u
<220> FEATURE:
<221> NAME/KEY: misc_feature
<222> LOCATION: (318)..(318)
<223> OTHER INFORMATION: n is a, c, g, t or u
<220> FEATURE:
<221> NAME/KEY: misc_feature
<222> LOCATION: (327)..(327)
<223> OTHER INFORMATION: n is a, c, g, t or u
<220> FEATURE:
<221> NAME/KEY: misc_feature
<222> LOCATION: (333)..(333)
<223> OTHER INFORMATION: n is a, c, g, t or u
<220> FEATURE:
<221> NAME/KEY: misc_feature
<222> LOCATION: (336)..(336)
<223> OTHER INFORMATION: n is a, c, g, t or u
<220> FEATURE:
<221> NAME/KEY: misc_feature
<222> LOCATION: (339)..(339)
<223> OTHER INFORMATION: n is a, c, g, t or u
<220> FEATURE:
<221> NAME/KEY: misc_feature
<222> LOCATION: (342)..(342)
<223> OTHER INFORMATION: n is a, c, g, t or u
<220> FEATURE:
<221> NAME/KEY: misc_feature
<222> LOCATION: (348)..(348)
<220> FEATURE:
<221> NAME/KEY: misc_feature
<222> LOCATION: (354)..(354)
<223> OTHER INFORMATION: n is a, c, g, t or u
<220> FEATURE:
<221> NAME/KEY: misc_feature
<222> LOCATION: (357)..(357)
<223> OTHER INFORMATION: n is a, c, g, t or u
<220> FEATURE:
<221> NAME/KEY: misc_feature
```

```
<222> LOCATION: (366)..(366)
<223> OTHER INFORMATION: n is a, c, g, t or u
<220> FEATURE:
<221> NAME/KEY: misc_feature
<222> LOCATION: (369)..(369)
<223> OTHER INFORMATION: n is a, c, g, t or u
<220> FEATURE:
<221> NAME/KEY: misc_feature
<222> LOCATION: (372)..(372)
<223> OTHER INFORMATION: n is a, c, g, t or u
<220> FEATURE:
<221> NAME/KEY: misc_feature
<222> LOCATION: (384)..(384)
<223> OTHER INFORMATION: n is a, c, g, t or u
<220> FEATURE:
<221> NAME/KEY: misc_feature
<222> LOCATION: (387)..(387)
<223> OTHER INFORMATION: n is a, c, g, t or u
<220> FEATURE:
<221> NAME/KEY: misc_feature
<222> LOCATION: (390)..(390)
<223> OTHER INFORMATION: n is a, c, g, t or u
<220> FEATURE:
<221> NAME/KEY: misc_feature
<222> LOCATION: (396)..(396)
<223> OTHER INFORMATION: n is a, c, g, t or u
<220> FEATURE:
<221> NAME/KEY: misc_feature
<222> LOCATION: (402)..(402)
<223> OTHER INFORMATION: n is a, c, g, t or u
<220> FEATURE:
<221> NAME/KEY: misc_feature
<222> LOCATION: (405)..(405)
<223> OTHER INFORMATION: n is a, c, g, t or u
<220> FEATURE:
<221> NAME/KEY: misc_feature
<222> LOCATION: (408)..(408)
<223> OTHER INFORMATION: n is a, c, g, t or u
<220> FEATURE:
<221> NAME/KEY: misc_feature
<222> LOCATION: (411)..(411)
<223> OTHER INFORMATION: n is a, c, g, t or u
<220> FEATURE:
<221> NAME/KEY: misc_feature
<222> LOCATION: (420)..(420)
<223> OTHER INFORMATION: n is a, c, g, t or u
<220> FEATURE:
<221> NAME/KEY: misc_feature
<222> LOCATION: (432)..(432)
<223> OTHER INFORMATION: n is a, c, g, t or u
<220> FEATURE:
<221> NAME/KEY: misc_feature
<222> LOCATION: (435)..(435)
<223> OTHER INFORMATION: n is a, c, g, t or u
<220> FEATURE:
<221> NAME/KEY: misc_feature
<222> LOCATION: (441)..(441)
<223> OTHER INFORMATION: n is a, c, g, t or u
<220> FEATURE:
<221> NAME/KEY: misc_feature
<222> LOCATION: (444)..(444)
<223> OTHER INFORMATION: n is a, c, g, t or u
<220> FEATURE:
<221> NAME/KEY: misc_feature
<222> LOCATION: (453)..(453)
<223> OTHER INFORMATION: n is a, c, g, t or u
<220> FEATURE:
<221> NAME/KEY: misc_feature
<222> LOCATION: (468)..(468)
<223> OTHER INFORMATION: n is a, c, g, t or u
<220> FEATURE:
<221> NAME/KEY: misc_feature
<222> LOCATION: (471)..(471)
<223> OTHER INFORMATION: n is a, c, g, t or u
<220> FEATURE:
<221> NAME/KEY: misc_feature
<222> LOCATION: (477)..(477)
<223> OTHER INFORMATION: n is a, c, g, t or u
<220> FEATURE:
```

-continued

```
<221> NAME/KEY: misc_feature
<222> LOCATION: (480)..(480)
<223> OTHER INFORMATION: n is a, c, g, t or u
<220> FEATURE:
<221> NAME/KEY: misc_feature
<222> LOCATION: (483)..(483)
<223> OTHER INFORMATION: n is a, c, g, t or u
<220> FEATURE:
<221> NAME/KEY: misc_feature
<222> LOCATION: (492)..(492)
<223> OTHER INFORMATION: n is a, c, g, t or u
<220> FEATURE:
<221> NAME/KEY: misc_feature
<222> LOCATION: (495)..(495)
<223> OTHER INFORMATION: n is a, c, g, t or u
<220> FEATURE:
<221> NAME/KEY: misc_feature
<222> LOCATION: (501)..(501)
<223> OTHER INFORMATION: n is a, c, g, t or u
<220> FEATURE:
<221> NAME/KEY: misc_feature
<222> LOCATION: (504)..(504)
<223> OTHER INFORMATION: n is a, c, g, t or u
<220> FEATURE:
<221> NAME/KEY: misc_feature
<222> LOCATION: (507)..(507)
<223> OTHER INFORMATION: n is a, c, g, t or u
<220> FEATURE:
<221> NAME/KEY: misc_feature
<222> LOCATION: (510)..(510)
<223> OTHER INFORMATION: n is a, c, g, t or u
<220> FEATURE:
<221> NAME/KEY: misc_feature
<222> LOCATION: (513)..(513)
<223> OTHER INFORMATION: n is a, c, g, t or u
<220> FEATURE:
<221> NAME/KEY: misc_feature
<222> LOCATION: (522)..(522)
<223> OTHER INFORMATION: n is a, c, g, t or u
<220> FEATURE:
<221> NAME/KEY: misc_feature
<222> LOCATION: (528)..(528)
<223> OTHER INFORMATION: n is a, c, g, t or u
<220> FEATURE:
<221> NAME/KEY: misc_feature
<222> LOCATION: (531)..(531)
<223> OTHER INFORMATION: n is a, c, g, t or u
<220> FEATURE:
<221> NAME/KEY: misc_feature
<222> LOCATION: (537)..(537)
<223> OTHER INFORMATION: n is a, c, g, t or u
<220> FEATURE:
<221> NAME/KEY: misc_feature
<222> LOCATION: (540)..(540)
<223> OTHER INFORMATION: n is a, c, g, t or u
<220> FEATURE:
<221> NAME/KEY: misc_feature
<222> LOCATION: (543)..(543)
<223> OTHER INFORMATION: n is a, c, g, t or u
<220> FEATURE:
<221> NAME/KEY: misc_feature
<222> LOCATION: (546)..(546)
<223> OTHER INFORMATION: n is a, c, g, t or u
<220> FEATURE:
<221> NAME/KEY: misc_feature
<222> LOCATION: (549)..(549)
<223> OTHER INFORMATION: n is a, c, g, t or u
<220> FEATURE:
<221> NAME/KEY: misc_feature
<222> LOCATION: (552)..(552)
<223> OTHER INFORMATION: n is a, c, g, t or u
<220> FEATURE:
<221> NAME/KEY: misc_feature
<222> LOCATION: (555)..(555)
<223> OTHER INFORMATION: n is a, c, g, t or u
<220> FEATURE:
<221> NAME/KEY: misc_feature
<222> LOCATION: (558)..(558)
<223> OTHER INFORMATION: n is a, c, g, t or u
```

-continued

```
<220> FEATURE:
<221> NAME/KEY: misc_feature
<222> LOCATION: (561)..(561)
<223> OTHER INFORMATION: n is a, c, g, t or u
<220> FEATURE:
<221> NAME/KEY: misc_feature
<222> LOCATION: (564)..(564)
<223> OTHER INFORMATION: n is a, c, g, t or u
<220> FEATURE:
<221> NAME/KEY: misc_feature
<222> LOCATION: (573)..(573)
<223> OTHER INFORMATION: n is a, c, g, t or u
<220> FEATURE:
<221> NAME/KEY: misc_feature
<222> LOCATION: (576)..(576)
<223> OTHER INFORMATION: n is a, c, g, t or u
<220> FEATURE:
<221> NAME/KEY: misc_feature
<222> LOCATION: (582)..(582)
<223> OTHER INFORMATION: n is a, c, g, t or u
<220> FEATURE:
<221> NAME/KEY: misc_feature
<222> LOCATION: (585)..(585)
<223> OTHER INFORMATION: n is a, c, g, t or u
<220> FEATURE:
<221> NAME/KEY: misc_feature
<222> LOCATION: (597)..(597)
<223> OTHER INFORMATION: n is a, c, g, t or u
<220> FEATURE:
<221> NAME/KEY: misc_feature
<222> LOCATION: (603)..(603)
<223> OTHER INFORMATION: n is a, c, g, t or u
<220> FEATURE:
<221> NAME/KEY: misc_feature
<222> LOCATION: (615)..(615)
<223> OTHER INFORMATION: n is a, c, g, t or u
<220> FEATURE:
<221> NAME/KEY: misc_feature
<222> LOCATION: (633)..(633)
<223> OTHER INFORMATION: n is a, c, g, t or u
<220> FEATURE:
<221> NAME/KEY: misc_feature
<222> LOCATION: (642)..(642)
<223> OTHER INFORMATION: n is a, c, g, t or u
<220> FEATURE:
<221> NAME/KEY: misc_feature
<222> LOCATION: (654)..(654)
<223> OTHER INFORMATION: n is a, c, g, t or u
<220> FEATURE:
<221> NAME/KEY: misc_feature
<222> LOCATION: (663)..(663)
<223> OTHER INFORMATION: n is a, c, g, t or u
<220> FEATURE:
<221> NAME/KEY: misc_feature
<222> LOCATION: (666)..(666)
<223> OTHER INFORMATION: n is a, c, g, t or u
<220> FEATURE:
<221> NAME/KEY: misc_feature
<222> LOCATION: (669)..(669)
<223> OTHER INFORMATION: n is a, c, g, t or u
<220> FEATURE:
<221> NAME/KEY: misc_feature
<222> LOCATION: (675)..(675)
<223> OTHER INFORMATION: n is a, c, g, t or u
<220> FEATURE:
<221> NAME/KEY: misc_feature
<222> LOCATION: (678)..(678)
<223> OTHER INFORMATION: n is a, c, g, t or u
<220> FEATURE:
<221> NAME/KEY: misc_feature
<222> LOCATION: (681)..(681)
<223> OTHER INFORMATION: n is a, c, g, t or u
<220> FEATURE:
<221> NAME/KEY: misc_feature
<222> LOCATION: (684)..(684)
<223> OTHER INFORMATION: n is a, c, g, t or u
<220> FEATURE:
<221> NAME/KEY: misc_feature
<222> LOCATION: (705)..(705)
```

-continued

```
<223> OTHER INFORMATION: n is a, c, g, t or u

<400> SEQUENCE: 10
gaygaygayt gyathgtngt ngartaytay athgtnacng aywsngcntt yacnaarmgn     60
ttyaarwsna aywsngcnyt nacnaaytay gtnacngtna tgttyacngg ngtncargar    120
ytnytngaya cnytnaayyt nggnathggn gtnmgnytny tnggngtnac nacnttyacn    180
garaaracng arccnwsntt yathaargay aayytnathc cnggnccncc ngcngcntty    240
gayccngayg tnytnathws ngcnatgwsn aartaytayt gyaaycayca racnggnytn    300
gcnaargaya cngayytnat httyytnath acngcnmgng gnatgggnga yccnmgngar    360
gayggnacng tngayathaa yacngcnggn athgcnaayw sngcnggngt ntgyaarccn    420
tgyttyaarw snggnathgc nacngaygay wsngaytaya aygarmgngt ngayacnytn    480
gcncaygarw sngtncayyt nytnggnwsn ccncaygayg gngarggncc naayytngtn    540
wsnytnggnw snccnggngc ngcnaaytgy ccngcnaarg cnggntayat hatgggnaay    600
mgnaaygaya argtnaayaa rtayaartty wsnaaytgya cnaaraartg ygtngartay    660
ytnytnwsna arccnacngc nwsntgyath ttycarcart gywsngay                 708
```